United States Patent
Wolfova et al.

(10) Patent No.: US 9,492,586 B2
(45) Date of Patent: Nov. 15, 2016

(54) DERIVATIVES OF HYALURONIC ACID CAPABLE OF FORMING HYDROGELS

(71) Applicant: Contipro Biotech s.r.o., Dolni Dobrouc (CZ)

(72) Inventors: Lucie Wolfova, Opava (CZ); Martin Pravda, Koci (CZ); Marcela Foglarova, Machov (CZ); Miroslava Nemcova, Chocen (CZ); Krzysztof Niedoba, Goleszow (PL); Vladimir Velebny, Zamberk (CZ)

(73) Assignee: Contipro Biotech s.r.o., Dolni Dobrouc (CZ)

( * ) Notice: Subject to any disclaimer, the term of this patent is extended or adjusted under 35 U.S.C. 154(b) by 217 days.

(21) Appl. No.: 14/381,091

(22) PCT Filed: Feb. 26, 2013

(86) PCT No.: PCT/CZ2013/000023
§ 371 (c)(1),
(2) Date: Aug. 26, 2014

(87) PCT Pub. No.: WO2013/127374
PCT Pub. Date: Sep. 6, 2013

(65) Prior Publication Data
US 2015/0000561 A1 Jan. 1, 2015

(30) Foreign Application Priority Data
Feb. 28, 2012 (CZ) .............................. PV 2012-136

(51) Int. Cl.
*C12P 19/26* (2006.01)
*A61L 27/20* (2006.01)
(Continued)

(52) U.S. Cl.
CPC ................ *A61L 27/20* (2013.01); *A61K 8/735* (2013.01); *A61L 15/28* (2013.01); *A61L 26/0023* (2013.01);
(Continued)

(58) Field of Classification Search
CPC ... A61L 27/10; A61L 15/28; A61L 26/0023; A61L 31/042; A61L 2430/06; A61L 2430/34; A61L 2430/03; A61K 8/735; A61K 2800/10; A61Q 19/00; A61Q 19/08
See application file for complete search history.

(56) References Cited

U.S. PATENT DOCUMENTS 3,720,662 A 3/1973 Tessler et al.
3,728,223 A 4/1973 Kaneko et al.
(Continued)

FOREIGN PATENT DOCUMENTS

CA 2512730 A1 7/2004
CH 628088 A5 2/1982
(Continued)

OTHER PUBLICATIONS

Lee et al. J. Controlled Release (2009) 134: 186-193.*
(Continued)

*Primary Examiner* — Susan Hanley
(74) *Attorney, Agent, or Firm* — Wood, Herron & Evans, L.L.P.

(57) ABSTRACT

The invention related to hyaluronic derivative according to formula (I), methods of preparation thereof and a hydrogel prepared obtained from the derivative and methods of preparation thereof. The hydrogel can be used in tissue engineering, cosmetics, medicine or regenerative medicine such as the forming of scaffolds for the treatment of articular cartilage or bone tissue defects.

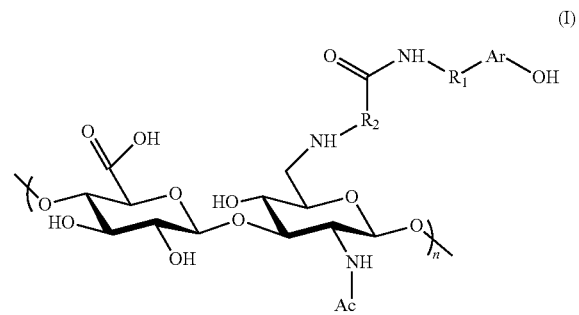

9 Claims, 1 Drawing Sheet

(51) Int. Cl.
  *A61K 8/73* (2006.01)
  *C08B 37/08* (2006.01)
  *A61L 15/28* (2006.01)
  *A61L 31/04* (2006.01)
  *A61L 26/00* (2006.01)
  *A61Q 19/00* (2006.01)
  *A61Q 19/08* (2006.01)

(52) U.S. Cl.
  CPC ............ *A61L 31/042* (2013.01); *A61Q 19/00* (2013.01); *C08B 37/0072* (2013.01); *A61K 2800/10* (2013.01); *A61L 2430/02* (2013.01); *A61L 2430/06* (2013.01); *A61L 2430/34* (2013.01); *A61Q 19/08* (2013.01)

(56) References Cited

U.S. PATENT DOCUMENTS

| | | | |
|---|---|---|---|
| 4,205,025 A | 5/1980 | Hart et al. |
| 4,258,134 A | 3/1981 | Yoshida et al. |
| 4,713,448 A | 12/1987 | Balazs et al. |
| 4,761,401 A | 8/1988 | Couchman et al. |
| 4,851,521 A | 7/1989 | Della Valle et al. |
| 4,965,353 A | 10/1990 | Della Valle et al. |
| 5,455,349 A | 10/1995 | Grasshoff et al. |
| 5,520,916 A | 5/1996 | Dorigatti et al. |
| 5,550,225 A | 8/1996 | Philippe |
| 5,616,568 A | 4/1997 | Pouyani et al. |
| 5,658,582 A | 8/1997 | Dorigatti et al. |
| 5,676,964 A | 10/1997 | Della Valle et al. |
| 5,690,961 A | 11/1997 | Nguyen |
| 5,824,335 A | 10/1998 | Dorigatti et al. |
| 5,868,973 A | 2/1999 | Muller et al. |
| 6,025,444 A | 2/2000 | Waki et al. |
| 6,075,066 A | 6/2000 | Matsuda et al. |
| 6,288,043 B1 | 9/2001 | Spiro et al. |
| 6,509,039 B1 | 1/2003 | Nies |
| 6,613,897 B1 | 9/2003 | Yatsuka et al. |
| 6,632,802 B2 | 10/2003 | Bellini et al. |
| 6,673,919 B2 | 1/2004 | Yui et al. |
| 6,683,064 B2 | 1/2004 | Thompson et al. |
| 6,719,986 B1 | 4/2004 | Wohlrab et al. |
| 6,902,548 B1 | 6/2005 | Schuler et al. |
| 6,953,784 B2 | 10/2005 | Thompson et al. |
| 7,214,759 B2 | 5/2007 | Pacetti et al. |
| 7,550,136 B2 | 6/2009 | Warner et al. |
| 7,680,038 B1 | 3/2010 | Gourlay |
| 2002/0026039 A1 | 2/2002 | Bellini et al. |
| 2002/0076810 A1 | 6/2002 | Radice et al. |
| 2003/0163073 A1 | 8/2003 | Effing et al. |
| 2003/0205839 A1 | 11/2003 | Bachrach |
| 2004/0101546 A1 | 5/2004 | Gorman et al. |
| 2004/0192643 A1 | 9/2004 | Pressato et al. |
| 2005/0266546 A1 | 12/2005 | Warner et al. |
| 2006/0046590 A1 | 3/2006 | Chu et al. |
| 2006/0084759 A1 | 4/2006 | Calabro et al. |
| 2006/0189516 A1 | 8/2006 | Yang et al. |
| 2006/0281912 A1 | 12/2006 | James et al. |
| 2007/0149441 A1 | 6/2007 | Aeschlimann et al. |
| 2007/0202084 A1 | 8/2007 | Sadozai et al. |
| 2008/0063617 A1 | 3/2008 | Abrahams et al. |
| 2008/0124395 A1 | 5/2008 | Chen et al. |
| 2009/0252810 A1 | 10/2009 | Tommeraas et al. |
| 2010/0172892 A1 | 7/2010 | Uvarkina et al. |
| 2010/0247908 A1 | 9/2010 | Velev et al. |
| 2010/0310631 A1 | 12/2010 | Domard et al. |
| 2010/0310853 A1 | 12/2010 | Schwiegk et al. |
| 2010/0316682 A1 | 12/2010 | Chen et al. |
| 2011/0200676 A1 | 8/2011 | Lin et al. |
| 2011/0263724 A1 | 10/2011 | Gurtner et al. |
| 2012/0245323 A1 | 9/2012 | Buffa et al. |
| 2012/0264913 A1 | 10/2012 | Buffa et al. |

FOREIGN PATENT DOCUMENTS

| | | |
|---|---|---|
| CN | 101897976 | 12/2010 |
| CN | 102154738 A | 8/2011 |
| CZ | 2006605 A3 | 4/2008 |
| CZ | 20070299 A3 | 2/2009 |
| CZ | 301899 B6 | 7/2010 |
| CZ | 302503 B6 | 6/2011 |
| CZ | 302504 B6 | 6/2011 |
| CZ | 302856 B6 | 12/2011 |
| CZ | 302994 B6 | 2/2012 |
| CZ | 20101001 A3 | 2/2012 |
| CZ | 20120537 A3 | 3/2014 |
| DE | 10331342 A1 | 2/2005 |
| EP | 0161887 A2 | 11/1985 |
| EP | 0216453 A2 | 4/1987 |
| EP | 0763754 A2 | 3/1997 |
| EP | 0554898 B1 | 5/1997 |
| EP | 1369441 A1 | 12/2003 |
| EP | 1454913 A1 | 9/2004 |
| EP | 1115433 B1 | 12/2004 |
| EP | 1538166 A1 | 6/2005 |
| EP | 1217008 B1 | 3/2006 |
| EP | 1826274 A1 | 8/2007 |
| EP | 1905456 A1 | 4/2008 |
| EP | 1607405 B1 | 5/2011 |
| EP | 2399940 A2 | 12/2011 |
| JP | 62104579 A | 5/1987 |
| JP | 63044883 A | 11/1988 |
| JP | H0214019 A | 1/1990 |
| JP | H0625306 A | 2/1994 |
| JP | 2004507586 A | 3/2004 |
| JP | 2007262595 A | 10/2007 |
| JP | 3975267 B2 | 12/2007 |
| JP | 2008208480 A | 9/2008 |
| JP | 2008295885 A | 12/2008 |
| JP | 2010138276 A | 6/2010 |
| KR | 20070118730 A | 12/2007 |
| KR | 20080062092 A | 7/2008 |
| NL | 9700003 A | 7/1997 |
| WO | 9311803 A1 | 6/1993 |
| WO | 9627615 A1 | 9/1996 |
| WO | 9808876 A1 | 3/1998 |
| WO | 9901143 A1 | 1/1999 |
| WO | 9957158 A1 | 11/1999 |
| WO | 0063470 A1 | 10/2000 |
| WO | 0134657 A1 | 5/2001 |
| WO | 0218448 A2 | 3/2002 |
| WO | 0218450 A1 | 3/2002 |
| WO | 0232913 A1 | 4/2002 |
| WO | 0248197 A1 | 6/2002 |
| WO | 02057210 A1 | 7/2002 |
| WO | 2005028632 A2 | 3/2005 |
| WO | 2006010066 A2 | 1/2006 |
| WO | 2006026104 A2 | 3/2006 |
| WO | 2006056204 A1 | 6/2006 |
| WO | 2007003905 A1 | 1/2007 |
| WO | 2007006403 A1 | 1/2007 |
| WO | 2007009728 A2 | 1/2007 |
| WO | 2007033677 A1 | 3/2007 |
| WO | 2008031525 A1 | 3/2008 |
| WO | 2008077172 A2 | 7/2008 |
| WO | 2009037566 A2 | 3/2009 |
| WO | 2009050389 A2 | 4/2009 |
| WO | 2009108100 A1 | 9/2009 |
| WO | 2009148405 A1 | 12/2009 |
| WO | 2010018324 A1 | 2/2010 |
| WO | 2010051783 A1 | 5/2010 |
| WO | 2010061005 A1 | 6/2010 |
| WO | 2010095049 A1 | 8/2010 |
| WO | 2010095052 A2 | 8/2010 |
| WO | 2010095056 A2 | 8/2010 |
| WO | 2010130810 A1 | 11/2010 |
| WO | 2010138074 A1 | 12/2010 |
| WO | 2011014432 A1 | 2/2011 |
| WO | 2011028031 A2 | 3/2011 |
| WO | 2011059325 A2 | 5/2011 |
| WO | 2011059326 A2 | 5/2011 |
| WO | 2011069474 A2 | 6/2011 |

(56) References Cited

FOREIGN PATENT DOCUMENTS

| WO | 2011069475 A2 | 6/2011 |
|---|---|---|
| WO | 2012089179 A1 | 7/2012 |
| WO | 2012146218 A1 | 11/2012 |
| WO | 2013056312 A1 | 4/2013 |
| WO | 2014023272 A1 | 2/2014 |

OTHER PUBLICATIONS

Matsushima, R. et al., "Photoreactions of Alkylated 2-Pyridones," J. Chem. Soc. Perkin Trans. 2 (1985) 1445-1448.

Mayol, L. et al., Amphiphilic hyaluronic acid derivatives toward the design of micelles for the sustained delivery of hydrophobic drugs, Carbohydrate Polymers, vol. 102, Feb. 1, 2014, pp. 110-116.

Mazzone, S. B., Mori, N., Bunnan, M., Palovich, M., Belmonte, K E. & Canning, B. J. (2006). Fluorescent styryl dyes FM 1-43 and FM2-10 are muscarinic receptor antagonists: intravital visualization of receptor occupancy. The Journal of Physiology, 575(1), 23-35.

McIntyre, J.E, "The Chemistry of Fibres," Studies in Chemistry No. 6, 1971, p. 15.

McTaggart, L.E. et al., "Assessment of polysaccharide gels as drug delivery vehicles," Int. J. Pharm. 1993, vol. 100,pp. 199-206.

Miller, R.J. et aL, Chemistry and Biology of Hyaluronan : Medicinal Uses of Modified Hyaluronate. Elsevier Ltd. 2004. 505-528.

Nevell, T.P. et al., "Cellulose Chemistry and its Applications," 1985, John Wiley & Sons, pp. 455-479.

Oh, E.J. et al., "Target specific and long-acting delivery of protein, peptide, and nukleotide therapeutics using hyaluronic acid derivatives," J. Controlled Release vol. 141, 2010, pp. 2-12.

Pal, K. et al., "Biopolymers in Controlled-Release Delivery Systems," Modern Biopolymer Science (2009) 519-557.

Park, Y.D. et al., Photopolymerized hyaluronic acid-based hydrogels and interpenetrating networks, Biomaterials (2003) 24:893-900.

Piluso, S. et al., "Hyaluronic acid-based hydrogels crosslinked by copper-catalyzed azide-alkyne cycloaddition with tailorable mechanical properties," International Journal of Artificial Organs (2011) 34:192-197, Abstract.

Prestwich, G.D., "Hyaluronic acid-based clinical biomaterials derived for cell and molecule delivery in regenerative medicine," Journal of Controlled Release (2011) 155:193-199.

Prestwich, G.D., internet article "Biomaterials from Chemically-Modified Hyaluronan", Feb. 26, 2001, 17 pages.

Qiu, Y. et al., "Environment-sensitive hydrogels for drug delivery," Advanced Drug Delivery Reviews (2001) 53:321-339.

Rao, K.V.R. et al., "Influence of Molecular Size and Water Solubility of the Solute on its Release from Swelling and Erosion Controlled Polymeric Matrices," Journal of Controlled Release (1990) 12:133-141.

Ritger, P.L. et al., "A Simple Equation for Description fo Solute Release I. Fickian and Non-Fickian Release from Non-Swellable Devices in the Form of Slabs, Spheres, Cylinders or Discs," Journal of Controlled Release (1987) 5:23-36.

Ritger, P.L. et al., "A Simple Equation for Description fo Solute Release II. Fickian and Anomalous Release from Swellable Devices," Journal of Controlled Release (1987) 5:37-42.

Rostovtsev, V.V. et al., "A Stepwise Huisgen Cycloaddition Process: Copper(I)-Catalyzed Regioselective 'Ligation' of Azides and Terminal Alkynes," Angew. Chem. Int. Ed. (2002) 41(14):2596-2599.

Rupprecht, A., Wet Spinning of Hyaluronic Acid. Preparation of Oriented Samples; Acta Chemica Scandinavica; 1979; 33; 779-780.

Sahiner, N. et al., "Fabrication and characterization of cross-linkable hydrogel particles based on hyaluronic acid: potential application in volcal fold regeneration", Journal of Biomaterials Science, Polymer Edition, vol. 19, Issue 2, pp. 223-243.

Schante C.E. et al. "Chemical modifications of hyaluronic acid for the synthesis of derivatives for a broad range of biomedical applications," Carbohydrate Polymers (2011) 85:469-489.

Scott, J.E. et al., "Periodate Oxidation of Acid Polysaccharides", Histochemie, Apr. 26, 1969, vol. 19, pp. 155-161.

Scott, J.E. et al., "Secondary and tertiary structures of hyaluronan in aqueous solution, investigated by rotary shadowing—electron microscopy and computer simulation," J. Biochem vol. 274, 1991, pp. 699-705.

Sedova, P. et al., "Preparation of hyaluronan polyaldehyde—a precursor of biopolymer conjugates," Carbohydrate Research (2013) 371:8-15.

Seidlits, S.K. et al., "The effects of hyaluronic acid hydrogels with tunable mechanical properties on neural progenitor cell differentiation" Biomaterials (2010) 31:3930-3940.

Shang, J. et al., "Chitosan-based electroactive hydrogel," Polymer (2008) 49:5520-5525.

Sheehan, J.K. et al., X-ray diffraction studies on the connective tissue polysaccharides; J. Mol. Biol. 1975; 91; 153-163.

Shen, Y. et al., Synthesis and characterization of low molecular weight hyaluronic acid-based cationic micelles for efficient siRNA delivery, Carbohydrate Polymers, vol. 77, No. 1, 2009, pp. 95-104.

Shimizu, M. et al., "Studies on hyaluronidase, chondroitin sulphatase, proteinase and phospholipase secreted by *Candida* species", Mycoses (1996) 39:161-167.

Sieburth, S.M. et al., "Fusicoccin Ring System by [4 + 4} Cycloaddition. 2. A Model Study," Tetrahedron Letters (1999) 40:4007-4010.

Sieburth, S.M. et al., "The [4+4] Cycloaddition and its Strategic Application in Natural Product Synthesis," Tetrahedron (1996) 52(18):6251-6282.

Slezingrova, K. et al., "Synteza a charakterizace palmitoyl hyaluronanu," Chemicke Listy (2012) 106:554-567.

Smeds, K.A. et al., "Photocrosslinkable polysaccharides for in situ hydrogel formation," J. Biomed. Mater. Res. (2001) 54:115-121.

Smejkalova, D., Hennannova, M. Sulakova. R. PrflSova. A., Kucerik, J., & Velebny, V., Structural and conformational differences of acylated hyaluronan modified in protic and aprotic solvent system. Carbohydrate Polymers (2012) 87 (2):1460-1466.

Staskus, P.W. et al., "Double-Stranded Structure for Hyaluronic Acid in Ethanol-Aqueous Solution As Revealed by Circular Dichroism of Oligomers," Biochemistry vol. 27, No. 5, 1988, pp. 1528-1534.

Svanovsky, E. et al., "The effect of molecular weight on the biodistribution of hyaluronic acid radiolabeled with 111-In after intravenous administration to rats," Eur. J. Drug Metab. Ph. 2008, vol. 33, No. 3, pp. 149-157.

Tankam, P.F. et al., "Alkynyl polysaccharides: synthesis of propargyl potato starch followed by subsequent derivatizations," Carbohydrate Research (2007) 342:2049-2060.

Tao, Y., Xu. J., Chen, M.. Bai, H., & Liu, X. Core cross-linked hyaluronan-styrylpyridinium micelles as a novel carrier for paclitaxel. (2012). Carbohydrate Polymers, 88(1), 118-124.

Testa, G. et al., "Influence of dialkyne structure on the properties of new click-gels based on hyaluronic acid," International Journal of Pharmaceutics (2009) 378:86-92.

Til, H.P., Falke, H. E., Prinsen, M. K., & Willems, M. I. (1997). Acute and Subacute Toxicity of Tyramine, Spermidine, Spermine, Putrescine and Cadaverine in Rats. Food and Chemical Toxicology, 35(3-4), 337-348.

Tornoe, C. et al., "Peptidotriazoles on Solid Phase: [1,2,3]-Triazoles by Regiospecific Copper(I)-Catalyzed 1,3-Dipolar Dycloadditions of Terminal Alkynes to Azides," J. Org. Chem. (2002) 67:3057-3064.

Um, I.C. et al., "Electro-Spinning and Electro-Blowing of Hyaluronic Acid, " Biomacromolecules (2004) 5:1428-1436.

van Bommel, K.J.C. et al., "Responsive Cyclohexane-Based Low-Molecular-Weight Hydrogelators with Modular Architecture," Angew. Chem. Int. Ed. (2004) 1663-1667.

Wang, J., Mongayt, D., & Torchilin, V. P. (2005). Polymeric Micelles for Delivery of Poorly Soluble Drugs: Preparation and Anticancer Activity In Vitro of Paclitaxel Incorporated into Mixed Micelles Based on Polyethylene Glycol)-Lipid conjugate and Positively Charged Lipids. Journal of Drug Targeting, 13(1), 73-80.

Wang, X. et al., "Formation of water-resistant hyaluronic acid nanofibers by blowing-assisted electro-spinning an dnon-toxic post treatments," Polymer vol. 46, No. 13, 2005, pp. 4853-4867.

(56) References Cited

OTHER PUBLICATIONS

Weng, L. et al., "In vitro and in vivo suppression of cellular activity by guanidinoethyl disulfied released from hydrogel microspheres componsed of partially oxidized hyaluronan and gelatin", Biomaterials, 2008, vol. 29, pp. 4149-4156.

Weng, L et al., "Self-crosslinkable hydrogels composed of partially oxidized hyaluronan and gelatin: In vitro and in vivo responses", Journal of Biomedical Materials Research Part A, Aug. 9, 2007, pp. 352-365.

Written Opinion in International Patent Application No. PCT/CZ2009/000131, mailed Apr. 9, 2010, 3 pgs.

Aldrich, Chem Files Synthetic Methods Oxidation (English translation), May 2005, vol. 5, No. 1 pp. 1-11.

Author unknown, Encyclopedia of Cellulose (English translation), Asakura Publishing Co., Ltd., pp. 155-156 (Nov. 10, 2000).

Office Action in U.S. Appl. No. 13/512,484, mailed Oct. 1, 2015, 8 pgs.

Office Action in U.S. Appl. No. 13/512,484, mailed Sep. 11, 2014, 8 pgs.

Office Action in U.S. Appl. No. 13/514,759, mailed Jul. 30, 2015, 12 pgs.

Office Action in U.S. Appl. No. 13/514,759, mailed Sep. 24, 2014, 10 pgs.

Office Action in U.S. Appl. No. 13/977,181, mailed Jan. 22, 2016, 8 pgs.

Office Action in U.S. Appl. No. 14/113,527, mailed Feb. 12, 2016, 11 pgs.

Huerta-Angeles, G. et al., "Synthesis of highly substituted amide hyaluronan derivatives with tailored degree of substitution and their crosslinking via click chemistry," Carbohydrate Polymers (2011) 84:1293-1300.

Huh, K.M. et al., "Hydrotropic polymer micelle system for delivery of paclitaxel," Journal of Controlled Release (2005) 101:59-68.

Hynes, W.L. et al., "Hyaluronidases of Gram-positive bacteria," FEMS Microbiology Letters (2000) 183:201-207.

Inanaga, J. et al., A Rapid Esterification by Means of Mixed Anhydride and Its Application to Large-ring Lactonization, Bulletin of the Chemical Society of Japan, vol. 52, No. 7, 1979, pp. 1989-1993.

International Preliminary Report on Patentability in International Patent Application No. PCT/CZ2010/000128 issued on Feb. 5, 2013.

International Preliminary Report on Patentability in International Patent Application No. PCT/CZ2010/000129, mailed Jun. 12, 2012, 5 pgs.

International Search Report (Partial)—Invitation to Pay Fees in International Application No. PCT/CZ2013/000063, 3 pgs.

International Search Report and Written Opinion in International Application No. PCT/CZ2013/000057, mailed Jul. 24, 2013, 7 pgs.

International Search Report and Written Opinion in International Patent Application No. PCT/CZ2010/000128, mailed Jun. 9, 2011.

International Search Report and Written Opinion in International Patent Application No. PCT/CZ2013/000063, mailed Apr. 23, 2015, 16 pgs.

International Search Report and Written Opinion in International Patent Application No. PCT/CZ2013/000091, mailed Oct. 31, 2013, 6 pgs.

International Search Report and Written Opinion in International Patent Application No. PCT/CZ2013/000116, dated Jan. 28, 2014, 8 pgs.

International Search Report in International Patent Application No. PCT/CZ2009/000131, mailed Apr. 9, 2010, 3 pgs.

International Search Report in International Patent Application No. PCT/CZ2010/000030, mailed Sep. 1, 2010, 3 pgs.

International Search Report in International Patent Application No. PCT/CZ2010/000128, mailed Jun. 9, 2011, 3 pages.

International Search Report in International Patent Application No. PCT/CZ2010/000129, mailed Jun. 15, 2011, 3 pages.

International Search Report in International Patent Application No. PCT/CZ2011/000126, mailed Apr. 12, 2012, 3 pages.

International Search Report in International Patent Application No. PCT/CZ2012/0000035, mailed Aug. 28, 2012, 3 pgs.

International Search Report in International Patent Application No. PCT/CZ2013/000156, mailed Apr. 4, 2014, 5 pgs.

International Search Report in International Patent Application No. PCT/CZ2013/000158, mailed Mar. 19, 2014, 3 pgs.

International Search Report in International Patent Application No. PCT/CZ2013/000155, mailed Feb. 19, 2014, 4 pgs.

International Search Report in International Patent Application No. PCT/CZ2013/000157, mailed Mar. 19, 2014, 3 pgs.

Jacoboni, I, "Hyaluronic Acid by Atomic Force Microscopy," Journal of Structural Biology vol. 126, 1999, pp. 52-58.

Jahn, M. et al., "The reaction of hyaluronic acid and its monomers glucuronic acid and N-acetylglucosamine, with reactive oxygen species", Carbohydrate Research, 1999, vol. 321, pp. 228-234.

Japanese Official Action (English language translation) in corresponding Japanese Patent Application No. 2014-506754, dated Jan. 22, 2015, 2 pgs.

Japanese Official Action (including English language translation) in Japanese Patent Application No. 2012-542356, mailed Oct. 3, 2014, 8 pages.

Japanese Official Action in Japanese Patent Application No. 2012-542355, mailed Oct. 17, 2014.

Jia, X.Q. et al., "Synthesis and Characterization of in Situ Cross-Linkable Hyaluronic Acid-Based Hydrogels with Potential Application for Vocal Fold Regeneration," Macromolecules (2004) 37:3239-3248.

Jiang, B. et al., "Study on TEMPO-mediated selective oxidation of hyaluronan and the effects of salt on the reaction kinetics", Carbohydrate Research, vol. 327, No. 4, Aug. 7, 2000, pp. 455-461.

Jou, Chi-Hsiung et al., "Biocompatibility and Antibacterial Activity of Chitosan and Hyaluronic Acid Immobilized Polyester Fibers," Journal of Applied Polymer Science vol. 104, No. 1, 2007, pp. 220-225.

Juhlin, L, Hyaluronan in skin; Journal of Internal Medicine; 1997; 242; 61-66.

Katritzky, A.R. et al., "Cycloaddition Reactions of Heteroaromatic Six-Membered Rings," Chem. Rev. (1989) 89:827-861.

Kawaguchi, Y. et al., "The relation between the adsorption behavior at the interface and the conformational changes in hyaluronates partially modified with various acyl chains," Carbohydrate Polymers (1995) 26:149-154.

Kedar, U. et al., Advances in polymeric micelles for drug delivery and tumor targeting, Nanomedicine Nanotechnology, Biology and Medicine, vol. 6, No. 6, 2010, pp. 714-729.

Kim, B. et al., "Complexation Phenomena in pH-Responsive Copolymer Networks with Pendent Saccarides," Macromol. (2002) 35:9545-9550.

Kim, T.G., Lee, H., Jang, Y., & Park, T. G. (2009). Controlled Release of Paclitaxel from Heparinized Metal Stent Fabricated by Layer-by-Layer Assembly of Polylysine and Hyaluronic Acid-g-Poly(lactic-co-glycolic acid) Micelles Encapsulating Paclitaxel. Biomacromolecules, 10(6), 1532-1539.

Korsmeyer, R.W. et al., "Mechanisms of solute release from porous hydrophilic polymers," International Journal of Pharmaceutics (1983) 15:25-35.

Kuo, J.W., "Practical Aspects of Hyaluronan Based Medical Products," 2006, CRC Press, Taylor & Francis Group, pp. 60-61.

Lapcik, L. Jr. et al., Chemicke Listy vol. 85, 1991, pp. 281-298.

Leach, J.B. et al. "Characterization of protein release from photocrosslinkable hyaluronic acid-polyethylene glycol hydrogel tissue engineering scaffolds," Biomaterials (2005) 26:125-135.

Leach, J.B. et al. "Photocrosslinked Hyaluronic Acid Hydrogels: Natural, Biodegradable Tissue Engineering Scaffolds," Biotechnol Bioeng. (2003) 82:578-589.

Lee K.Y. et al. "Electrospinning of polysaccharides for regenerative medicine," Advanced Drug Delivery Reviews (2009) 61:1020-1032.

Lee S.A. et al. Spectroscopic studies of the physical properties of hyaluronate films: the origin of the phase transition; Carbohydrate Polymers; 1995; 28; 61-67.

(56) References Cited

OTHER PUBLICATIONS

Li J., Huo, M., Wang, J., Zhou, J., Mohammad, J. M., Zhang, Y., Zhu. Q., Waddad, A. Y., & Zhang, Q. (2012). Redox-sensitive micelles self-assembled from amphiphilic hyaluronic acid-deoxycholic acid conjugates for targeted intracellular delivery of paclitaxel. Biomaterials, 33(7), 2310-2320.
Linhardt, R.J. et al., "Polysaccharide lyases," Applied Biochemistry and Biotechnology (1986) 12:135-176.
Linhartova, B., Nanovlakna na bazi hyaluronanu, Bakalarska prace, Vysoke uceni technicke v Brne, 2008.
Liu, Yanchun et al., "Biocompatibility and stability of disulfide-crosslinked hyaluronan films," Biomaterials vol. 26, No. 23, 2005, pp. 4737-4746.
Liu, Yanhua et al., Dual targeting folate-conjugated hyaluronic acid polymeric micelles for paclitaxel delivery, International Journal of Pharmaceutics, vol. 421, No. 1, 2011, pp. 160-169.
Luo, Yanfeng et al., "Novel amphoteric pH-sensitive hydrogels derived from ethylenediaminetetraacetic dianhydride, butanediamine and amino-terminated poly(ethylene glycol): Design, synthesis and swelling behavior," European Polymer Journal (2011) 47:40-47.
Malkoch, M. et al., "Synthesis of well-defined hydrogel networks using Click chemistry," Chem. Commun. (2006) 2774-2776.
Aldrich, Chem Files Synthetic Methods Oxidation, May 2005, vol. 5, No. 1 pp. 1-11.
Angelin, M. et al., "Direct, Mild, and Selective Synthesis of Unprotected Dialdo-Glycosides," European Journal of Organic Chemistry, Jan. 1, 2006, pp. 4323-4326.
Armstrong, D.C. et al., "Culture Conditions Affect the Molecular Weight Properties of Hyaluronic Acid Produced by *Streptococcus zooepidemicus*," Appl. Environ. Microbiol. (1997) 63(7):2759-2764.
Atkins, E.D.T. et al., "The Conformation of the Mucopolysaccharides," J. Biochem vol. 128, 1972, pp. 1255-1263.
Atkins, E.D.T. et al., "The Molecular Structure of Hyaluronic Acid," Biochemical Journal vol. 125, No. 4, 1971, p. 92.
Author unknown, "Readily Accessible 12-I-51 Oxidant for the Conversion of Primary and Secondary Alcohols to Aldehydes and Ketones," Journal of Organic Chemistry, 1983, vol. 84, pp. 4155-4156.
Author unknown, Encyclopedia of Cellulose, Asakura Publishing Co., Ltd., pp. 155-156 (Nov. 10, 2000).
Bakke, M. et al., "Identification, characterization, and molecular cloning of a novel hyaluronidase, a member of glycosyl hydrolase family 16, from *Penicillium* spp.," FEBS Letters (2011) 585(1):115-120.
Banerji, S. et al., Structures of the Cd44-hyaluronan complex provide insight into a fundamental carboxyhydrate-protein interaction; Nature structural and molecular biology; 2007; 14; 234-239.
Bezakova, Z. et al., "Effect of microwave irradiation on the molecular and structural properties of hyaluronan," Carbohydrate Polymers, vol. 73, No. 4, 2008, pp. 640-646.
Boyer, I. J. (1989). Toxicity of dibutyltin, tributyltin and other organotin compounds to humans and to experimental animals. Toxicology, 55(3), 253-298.
Burdick, J.A. et al. "Controlled Degradation and Mechanical Behavior of Photopolymerized Hyaluronic Acid Networks," Biomacromolecules (2005) 6:386-391.
Burdick, J.A. et al., "Hyaluronic Acid Hydrogels for Biomedical Applications," Adv. Mater. (2011) 23:H41-H56.
Burke, J., Solubility Parameters: Theory and Application, The Book and Paper Group Annual, vol. Three, 1984, 62 pgs.
Chen, L. et al., "Synthesis and pH sensitivity of carboxyymethyl chitosan-based polyampholyte hydrogel for protein carrier matrices," Biomaterials (2004) 25:3725-3732.
Cornwell, M.J. et al., "A one-step synthesis of cyclodextrin monoaldehydes", Tetrahedron Letters, vol. 36, No. 46, Nov. 13, 1995, pp. 8371-8374.
Crescenzi, V. et al., "Novel Hydrogels via Click Chemistry: Synthesis and Potential Biomedical Applications," Biomacromolecules (2007) 8:1844-1850.
Czech Search Report in Czech Patent Application No. PV 2010-1001, dated Sep. 27, 2011, 1 pg.
Czech Search Report in Czech Patent Application No. PV 2011-241, dated Nov. 30, 2011, 1 pg.
Czech Search Report in Czech Patent Application No. PV 2012-136, dated Sep. 18, 2012, 3 pgs.
Czech Search Report in Czech Patent Application No. PV 2012-282, dated Jan. 30, 2013, 1 pg.
Czech Search Report in Czech Patent Application No. PV 2012-306, dated Feb. 11, 2013, 1 pg.
Czech Search Report in Czech Patent Application No. PV 2012-664, dated May 24, 2013, 3 pgs.
Czech Search Report in Czech Patent Application No. PV 2012-842, dated Aug. 19, 2013, 3 pgs.
Czech Search Report in Czech Patent Application No. PV 2012-843, dated Aug. 20, 2013, 1 pg.
Dilling, W.L. et al., "Organic Photochemistry. XII. The Photodimerization and Photoisomerization of 2-Pyridone and Its Monochloro Derivatives," Mol. Photochem. (1973) 5(4):371-409.
Ding, B. et al., "TEMPO-mediated selective oxidation of substituted polysaccharides—an efficient approach for the determination of the degree of substitution at C-6", Carbohydrate Research, vol. 343, No. 18, Dec. 8, 2008, pp. 3112-3116.
Donati, A. et al., "Solution Structure of Hyaluronic Acid Oligomers by Experimental and Theoretical NMR, and Molecular Dynamics Simulation," Biopolymers vol. 59, 2001, pp. 434-445.
Dumitriu, S., "Characterization and Properties of Hyaluronic Acid (Hyaluronan)," by M. Milas et al., Chap. 22 of Polysaccharides: Structural Diversity and Functional Versatility, 1998, Marcel Dekker Inc., pp. 535-549.
Eenschooten, C. et al., Preparation and structural characterisation of novel and versatile amphiphilic octenyl succinic anhydride-modified hyaluronic acid derivatives, Carbohydrate Polym Ers, vol. 79, No. 3, 2010, pp. 597-605.
El-Sherbiny, I.M. et al., "Poly(ethylene glycol)-carboxymethyl chitosan-based pH-responsive hydrogels: photo-induced synthesis, characterization, swelling, and in vitro evaluation as potential drug carriers," Carbohydrate Research (2010) 345:2004-2012.
Elander, R.P., "Industrial production of β-lactam antibiotics," Applied Microbiology and Biotechnology (2003) 31:385-392.
European First Official Action in European Patent Application no. 10812840.6-1306, mailed Jul. 2, 2013, 10 pages.
European Second Official Action in European Patent Application No. 10812840.6-1306, mailed Sep. 24, 2014.
Feng, Qian et al., Gaofenzi Cailiao Kexue Yu Gongcheng vol. 20 No. 1, 2004, pp. 146-148.
Ferrero, C. et al., "Fronts movement as a useful tool for hydrophilic matrix release mechanism elucidation," International Journal of Pharmaceutics (2000) 202:21-28.
Ferruti, P. et al., "Novel Poly(amido-amine)-Based Hydrogels as Scaffolds for Tissue Engineering," Macromol. Biosci. (2005) 5:613-622.
Funakoshi, T. et al., "Novel chitosan-based hyaluronan hybrid polymer fibers as a scaffold in ligament tissue engineering," Journal of Biomedical Materials Reasearch, Part A, vol. 74A, No. 3, 2005, pp. 338-346.
Gibby, W.A., M.D., "Cross-Linked DTPA Polysaccharides for Magnetic Resonance Imaging, Synthesis and Relaxation Properties," Invest. Radiol. 1989, vol. 24, pp. 302-309.
Gong, J. et al., (2012). Polymeric micelles drug delivery system in oncology. Journal of Controlled Release, 159(3), 312-323.
Guillaumie, F. et al., Comparative studies of various hyaluronic acids produced by microbial fermentation for potential topical ophthalmic applications. Journal of Biomedical Materials Research Part A; 2009; 1421-1430.
Gupta, P. et al., "Hydrogels: from controlled release to pH-respoonsive drug delivery," Drug Discovery Today (2002) 7(10):569-579.

(56) References Cited

OTHER PUBLICATIONS

Hasegawa, T. et al., "'Click chemistry' on polysaccharides: a convenient, general, and monitorable approach to develop (1-3)-β-D-glucans with various functional appendages," Carbohydrate Research (2006) 341:35-40.
Hoffman, A.S., "'Intelligent' Polymers in Medicine and Biotechnology," Artificial Organs 19(5):458-467.
Hofmann, H. et al., "Conformational Changes of Hyaluronic Acid in Acid Medium," Albrecht Von Graefe's Archive for Clinical and Experimental Opthamology vol. 198, No. 1, 1976, pp. 95-100.
Holten, K.B. et al., "Appropriate Prescribing of Oral Beta-Lactam Antibiotics," American Family Physician (2000) 62 (3):611-620.
Akkara, J. A.; Senecal , K. J.; Kaplan, D. L, Synthesis and characterization of polymers produced by horseradish peroxidase in dioxane. Journal of Polymer Science Part A: Polymer Chemistry 1991, 29 (11), 1561-1574.
Benedetti, L; Cortivo, R.; Berti, T.; Berti, A.; Pea, F.; Mazzo, M.; Moras, M.; Abatangelo, G., Biocompatibility and biodegradation of different hyaluronan derivatives (Hyaff) implanted-in rats. Biomaterials 1993, 14 (15), 1154-1160.
Burner, U.; Obinger, C., Transient-state and steady-state kinetics of the oxidation of aliphatic and aromatic thiols by horseradish peroxidase. FEES Letters 1997, 411 (2-3), 269-274.
Darr, A.; Calabro, A., Synthesis and characterization of tyramine-based hyaluronan hydrogels. Journal of Materials Science: Materials in Medicine 2009, 20 (1), 33-44.
Dunford, H. B.; Cotton, M. L., Kinetics of the oxidation of p-aminobenzoic acid catalyzed by horseradish peroxidase compounds I and II. J Biol Chem 1975, 250 (8), 2920-32.
Ghan, R.; Shutava, T.; Patel, A.; John, V. T.; Lvov, Y., Enzyme-Catalyzed Polymerization of Phenols within Polyelectrolyte Microcapsules. Macromolecules 2004, 3 7 (12), 4519-4524.
Gilabert, M. A.; Hiner, A. N.; Garcia-Ruiz, P. A.; Tudela, J.; Garcia-Molina, F.; Acosta, M.; Garcia-Canovas, F.; Rodriguez-Lopez, J. N., Differential substrate behaviour of phenol and aniline derivatives during oxidation by horseradish peroxidase: kinetic evidence for a two-step mechanism. Biochim Biophys Acta 2004, 1699 (1-2), 235-43.
Gilabert, M. A.; Phenoll, L. G.; Garcia-Molina, F.; Garcia-Ruiz, P. A.; Tudela, J.; Garcia-Canovas, F.; Rodriguez-Lopez, J. N., Stereospecificity of horseradish peroxidase. Biol Chem 2004, 385 (12), 1177-84.
Gilabert, M. A.; Phenoll, L. G.; Garcia-Molina, F.; Tudela, J.; Garcia-Canovas, F.; Rodriguez-Lopez, J. N., Kinetic characterization of phenol and aniline derivates as substrates of peroxidase. Biol Chem 2004, 385 (9), 795-800.
Hewson, W. D.; Dunford, H. B., Oxidation of p-cresol by horseradish peroxidase compound I. J Biol Chem 1976, 251 (19), 6036-42.
Hewson, W. D.; Dunford, H. B., Stoichiometry of the reaction between horseradish peroxidase and p-cresol. J Biol Chem 1976, 251(19), 6043-52.
Higashimura, H.; Kobayashi, S., Oxidative Polymerization. John Wiley & Sons, Inc. Olefin Fibers (2002) 10:740-764.
Jin, R.; Hiemstra, C.; Zhong, Z.; Feijen, J., Enzyme-mediated fast in situ formation of hydrogels from dextran-tyramine conjugates. Biomaterials 2007, 28 (18), 2791-2800.
Job, D.; Dunford, H. B., Substituent effect on the oxidation of phenols and aromatic amines by horseradish peroxidase compound I. Eur J Biochem 1976, 66 (3), 607-14.
Kalyanaraman, B.; Felix, C. C.; Sealy, R. C., Peroxidatic oxidation of catecholamines. A kinetic electron spin resonance investigation using the spin stabilization approach. Journal of Biological Chemistry 1984, 259 (12), 7584-7589.
Lee, F.; Chung, J. E.; Kurisawa, M., An injectable enzymatically crosslinked hyaluronic acid-tyramine hydrogel system with independent tuning of mechanical strength and gelation rate. Soft Matter 2008, 4, 880-887.
Patel, P. K.; Monda!, M. S.; Modi, S.; Behere, D. V., Kinetic studies on the oxidation of phenols by the horseradish peroxidase compound II. Biochim Biophys Acta 1997, 1339 (1), 79-87.
Shutava, T.; Zheng, Z.; John, V.; Lvov, Y., . Microcapsule modification with peroxidase-catalyzed phenol polymerization. Biomacromolecules 2004, 5 (3), 914-21.
Slaughter, B. V.; Khurshid, S. S.; Fisher, 0. Z.; Khademhosseini, A.; Peppas, N. A., Hydrogels in Regenerative Medicine. Advanced Materials 2009, 21 (32-33), 3307-3329.
Tan, H.; Chu, C. R.; Payne, K. A.; Marra, K. G., Injectable in situ forming biodegradable chitosan-hyaluronic acid based hydrogl fr cartilage tissue engineering. Biomaterials 2009, 30 (13), 2499-2506.
Tonelli, A. E., Effects of crosslink density and length on the number of intramolecular crosslinks (defects) introduced into a rubbery network. Polymer 1974, 15 (4), 194-196.
Uyama, H.; Kobayashi, S., Enzymatic Synthesis of Polyphenols. Current Organic Chemistry 2003, 7, 1387-1397.
Veitch, N. C., Horseradish peroxidase: a modem view of a classic enzyme. Phytochemistry 2004, 65 (3), 249-259.
Won, K.; Kim, Y. H.; An, E. S.; Lee, Y. S.; Song, B. K., Horseradish Peroxidase-. Catalyzed Polymerization of Cardanol in the Presence of Redox Mediators. Biomacromolecules 2003, 5 (1), 1-4.
Xu, Y.-P.; Huang, G.-L.; Yu, Y.-T., Kinetics of phenolic polymerization catalyzed by peroxidase in organic media. Biotechnology and Bioengineering 1995, 47 (1), 117-119.
Written Opinion in International Patent Application No. PCT/CZ2011/000126, mailed Apr. 12, 2012, 4 pgs.
Written Opinion in International Patent Application No. PCT/CZ2012/000035, mailed Aug. 28, 2012, 4 pgs.
Written Opinion in International Patent Application No. PCT/CZ2013/000023, dated Aug. 9, 2013, 3 pgs.
Written Opinion in International Patent Application No. PCT/CZ2013/000156, mailed Apr. 4, 2014, 7 pgs.
Written Opinion in International Patent Application No. PCT/CZ2013/000158, mailed Mar. 19, 2014, 7 pgs.
Written Opinion in International Patent Application No. PCT/CZ2010/000030, mailed Sep. 1, 2010, 4 pgs.
Written Opinion in International Patent Application No. PCT/CZ2013/000155, mailed Feb. 19, 2014, 6 pgs.
Written Opinion in International Patent Application No. PCT/CZ2013/000157, mailed Mar. 19, 2014, 6 pgs.
Yamane, Shintaro et al., "Feasibility of chitosan-based hyaluronic acid hybrid biomaterial for a novel scaffold in cartilage tissue engineering," Biomaterials vol. 26, No. 6, 2005, pp. 611-619.
Yao, F. et al., "A Novel Amphoteric, pH-Sensitive, Biodegradable Poly[chitosan-g-(L-lactic-co-citric) acid] Hydrogel," Journal of Applied Polymer Science (2003) 89:3850-3854.
Yeom, Junseok et al., "Effect of Cross-Linking Reagents for Hyaluronic Acid Hydrogel Dermal Fillers on Tissue Augmentation and Regeneration," Bioconjugate Chemistry (2010) 21(2)240-247.
Zhong, S.P. et al., "Biodegradation of hyaluronic acid derivatives by hyaluronidase," Biomaterials vol. 15, No. 5, 1994, pp. 359-365.

* cited by examiner

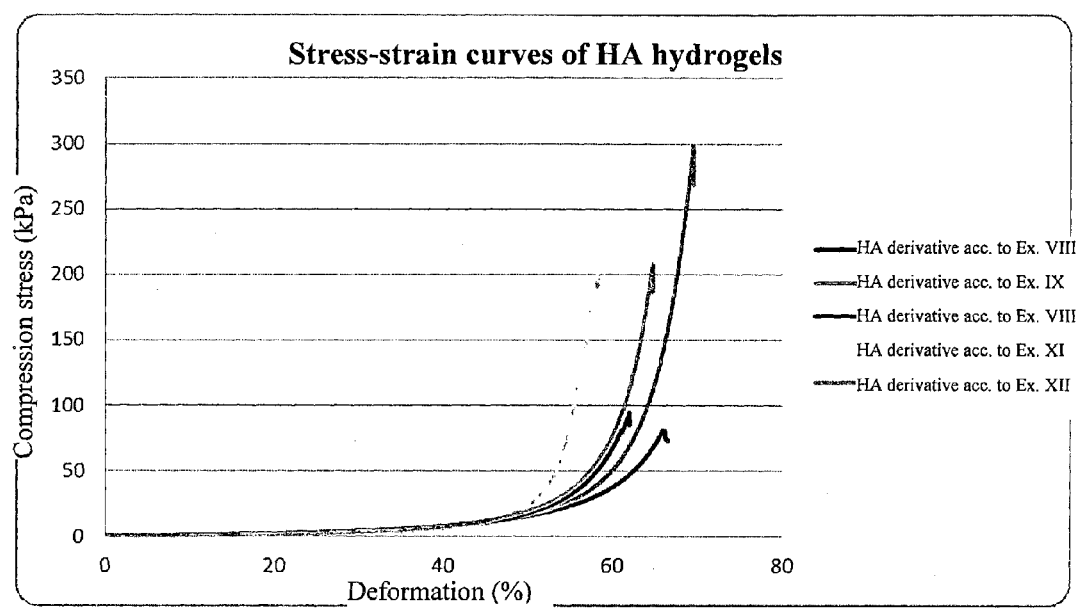

DERIVATIVES OF HYALURONIC ACID CAPABLE OF FORMING HYDROGELS

FIELD OF THE ART

The invention relates to a new hyaluronan acid derivative which is suitable for the preparation of hydrogels, and a method of preparation thereof. Further it relates to hydrogels based on said derivative, properties thereof, use and method of preparation thereof.

STATE OF THE ART

Hyaluronan is a polysaccharide consisting of disaccharidic units composed of D-glucuronic acid and D-N-acetyl-glucosamine which are bound by alternating β-1,4 and β-1,3 glycosidic bonds. The weight average molecular weight (if molecular weight is spoken of hereinafter, it will always be the weight average molecular weight) in vivo is within the range of 3 kDa-20 MDa. It is a polysaccharide which is easily soluble in an aqueous medium in which it forms highly viscous solutions, depending on its molecular weight and concentration.

Hydrogels are materials which are formed in water by an insoluble network of at least partially hydrophilic polymers[1]. There are several ways how to produce an insoluble network from an initially hydrophilic polymer. It is polymer hydrophobization[2] or the use of a water-soluble polymer derivative bearing reactive functional groups which may take part in further chemical reactions leading to the formation of a 3-dimensional polymer network[3-5].

The preparation of soluble hyaluronan derivatives and the following crosslinking thereof has been described by a number of authors[3-6]. In the past, the use of phenol hyaluronan derivative for crosslinking reactions and preparation of hydrogels have been described as well. Calabro et. al.[4, 7, 8] disclose the method of the preparation of phenol hyaluronan derivatives by means of a reaction of carboxyls which are present within the structure of hyaluronan D-glucuronic acid with aminoalkyl derivatives of phenol. This reaction produces hyaluronan amides. The crucial feature for the proceeding of said synthesis is the activation of the hyaluronan carboxyl for which the reaction with dehydrating agents of carbodiimide type (such as EDC) is used. The most frequently used aminoalkyl phenol is tyramine[6].

In general, crosslinking of phenol hyaluronan derivatives is initiated by adding a peroxidase (such as horseradish peroxidase—HRP) and a diluted hydrogen peroxide solution. The horseradish peroxidase (Horseradish peroxidase, HRP, E.C.1.11.1.7) is nowadays widely used as a catalyst of organic and biotransformation reactions[9-13]. It is characterised by a very broad substrate specificity and therefore, it is capable of oxidising a number of both organic and inorganic compounds[13-15].

It is an enzyme comprising hem containing iron, as a prosthetic group. The iron has the oxidation degree (III) in the non-activated state of the enzyme. The reaction with peroxides leads to the formation of an intermediate which is called HRP-I. The hem iron $Fe^{(III)}$ is oxidised to oxyferryl group ($Fe^{(IV)}=O$) and at the same time, a cationic π-radical on the porphyrin cycle is formed. Such an activated enzyme is able to form complexes with the molecules of the substrate which, during this interaction, undergoes oxidation.[14, 16-18]

The conversion of the oxidated enzyme back to the initial form thereof proceeds in two steps. In the first step, a reaction between the substrate molecule (S) and HRP-I takes place, giving rise to the substrate radical (R·) and a partially reduced form of the enzyme HRP-II. HRP-II still retains the oxyferryl group ($Fe^{(IV)}=O$) but it does not contain the porphyrin π-radical anymore. During the transition of an electron to the porphyrin radical one H⁺ is taken over by the protein at the same time. HRP-II undergoes the reaction with the substrate again, giving rise to R·. The oxyferryl group ($Fe^{(IV)}=O$) is reduced back to $Fe^{(III)}$ during this reaction. This process is associated with the transfer of 2H⁺ to the oxygen of oxyferryl group. One proton originates from the substrate (or solvent), the other form the protein. This results in the formation of a water molecule (Equation I and Scheme I).

Basic description of the mechanism of catalysis of substrate oxidation by means of HRP     Equation I

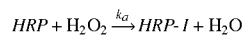
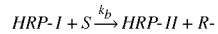
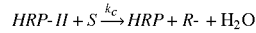
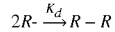

The resulted radicals of the substrate are in a number of cases able to interact together, forming dimers R—R. This process is not affected enzymatically anymore and is related to the stability and reactivity of the resulted radicals.[14, 16-26]

Therefore, in case of an enzymatic crosslinking reaction of the phenol derivative of polysaccharide, the substrate (phenol—reactive ligand bound to the polymer) is transformed by an enzyme to a reactive radical. This radical can then react with another phenol radical, forming dityramine. Supposing a free mobility of the substrate (ligand) molecules of the enzymatic reaction and the proceeding of the reaction exactly copying the equation I, the enzyme should gradually transform (provided a sufficient amount of peroxide is used) all the substrate molecules to the reactive radicals and these should all gradually undergo dimerisation (or oligomerisation), if a sufficiently long reaction time is provided. In case of linking the substrate (ligand) to the polymer, the crosslinking degree of the polymer should always reach the same value, even though the time for reaching this value would differ depending on the amount of the enzyme used. In practice it is different though. The literature[27] discloses in detail the relationships between the expected ratio of intramolecular and intermolecular crosslinking and the molecular weight of the polymer segments between the crosslinking locations (crosslinking density, the distance between the network nodes), while intramolecular interactions leading to the crosslinking are indicated as elastically non-effective, compared to intermolecular crosslinking.

Further, it is known from the literature that in case of using the phenol derivatives of HA, the amount of the enzyme affects not only the speed of the crosslinking reaction but also significantly affects the resulting mechanical properties of the hydrogels[4, 6, 7, 28]. The literature states that by rheologic measurements it has been found out that the modulus of shear (G') is higher if a higher concentration of the enzyme is used. The reason of this phenomenon, according to the authors, is a higher crosslinking density of the hydrogels. If a maximally firm hydrogel is to be prepared, the crosslinking reaction must proceed at a relatively high concentration of peroxidase, and therefore also faster. However, too fast proceedings of the reaction can then lead to the formation of a non-homogenous crosslinked hydrogel. There may then appear locations in the samples which are not crosslinked at all. Moreover, too fast proceedings of the reaction may also cause problems when placing the gel to the location of the final application thereof and the like.

The cause thereof is a small distance of the reactive centre from the basic polymer chain. The low mobility of the ligand decreases the probability of an effective collision of the ligand radicals to form dityramine. Therefore, if there is a low concentration of the enzyme within the system, small amount of reactive ligand forms may form in a time unit. Thus the crosslinking reaction proceeds slowly and is a little effective.

Park et. al.[29] tried to increase the reactivity of the ligands bound to the polymer by inserting a suitable spacer between the reactive ligand and the polymer chain. The document discloses insertion of a hydrophilic chain between the polysaccharide chain and the phenol or aniline ring in order to increase the reactivity of these substitutes. The main reason for introducing the hydrophilic chain into the structure of polymer was improving the solubility thereof and improving the accessibility of the reactive centres (phenol or aniline ring). An easier spatial accessibility of the reactive centres increases the probability of the reaction between the ligands. Most frequently, while maintaining the same enzyme activity, this step leads to a higher substitution degree, a higher concentration and better homogeneity of the hydrogel crosslinking. Moreover, according to the author, thanks to the introduction of this hydrophilic chain into the hydrogel structure, the biostability and mechanical properties of the hydrogel are increased. However, Park et al. use as a "spacer" a hydrophilic polymer PEG having the molecular weight of 3500 Da, and therefore, in the end it is rather a copolymer. However, such an intervention to the hydrogel structure, even in a low substitution degree, leads to significant changes of physical properties of the original polymer. Moreover, in case of hyaluronan, a higher crosslinking concentration leads to an increased hardness of the hydrogel, but at the same time it also leads to an increased fragility thereof, which is undesirable for the intended use in the tissue engineering. When a material designated for scaffolds, for example, but not only, for scaffolds for articular cartilage, is concerned, a stress is laid on the sufficient strength and resistance thereof, while a material which is fragile is irreversibly deformed at a higher load and in case of hydrogels, even a total destruction thereof occurs.

SUMMARY OF THE INVENTION

The aim of the invention therefore is to find a material which would be sufficiently strong and at the same time tenacious and which would not exhibit any significant changes of biological and physical properties compared to the original polymer. The strength of the hydrogel based on hyaluronan may generally be increased by increasing the crosslinking concentration, such as by increasing the concentration of the polymer in the solution from which the hydrogel is formed, or by increasing the substitution degree of the polymer. However, in the state of the art in case of hyaluronan both of these methods have led also to an increased fragility of the resulting hydrogel which significantly limits the possible uses of the hydrogel.

The problem that is solved by this invention consists in finding such derivatives that would lead to an increased ligand reactivity and an increased hydrogel strength, while maintaining the physical and biological properties of the original polymer. Surprisingly, it was found out that by introducing a relatively short spacer (having the molecular weight of approximately 130 Da) according to the invention between the reactive ligand and HA results in a significant increase of tenacity of the final hydrogels already at a very low substitution degree.

Therefore, in one aspect the invention relates to a HA derivative bearing reactive ligands bound via hydrophobic spacers, with the aim of increasing the mobility of ligands and thus increasing the probability of an effective collision thereof, even in case of a low concentration thereof (low substitution degree and low enzyme activity). It was found out that in spite of a very low weight abundance of the spacer within the hydrogel, making e.g. only 0.01 to 0.02%, a significant increase of tenacity and strength of the hydrogel is achieved compared to a hydrogel based on an analogous HA derivative without an inserted spacer (i.e. identical concentration, molar weight and degree of substitution/crosslinking). Therefore, the invention relates to this new hyaluronan derivative suitable for the preparation of hydrogels and a method of preparation thereof. Further, it relates to hydrogels based on this derivative, the use thereof and the method of preparation thereof.

The hydrogel is prepared by a method using crosslinking of the chains of the modified hyaluronan by means of a reaction that is catalyzed by horseradish peroxidase or analogues thereof. Suitable hyaluronan derivatives contain in their structure phenol or heteroaryl phenol rings covalently bound to the basic polysaccharide chain. The crosslinking procedure may be described as a cascade of consecutive chemical reactions which start with forming the reactive forms of oxygen (ROS) within the system. These are added to the mixture or their formation is enabled by the presence of chemical compounds which serve as a "generator" thereof. ROS activate the enzyme peroxidase or analogues thereof which subsequently catalyse the dimerization (or oligomerization) of aromatic or heteroaromatic rings present within the structure of the hyaluronan derivative. This leads to the formation of a three-dimensional polymer network.

According to the invention, hyaluronan modified by binding a ligand containing aminoalkyl phenol or aminoalkyl heteroaryl phenol (e.g. tyramine, 5-hydroxy tryptophane, serotonin) is used for the preparation of this hydrogel. The hyaluronan derivatives described in this invention contain a ligand which is bound to the polysaccharide by means of a spacer. The presence of this spacer within the structure of the HA derivative leads, thanks to its flexibility, to an increase of elasticity and freedom of possibilities of conformational arrangement of the participating polymer segments, and thus also the possibility of dissipation of deformation energy. The introduction of a spacer also increases the distance of the reactive aromatic centre (phenol, heteroaryl phenol) from the basic polymer chain, improves the accessibility thereof for an interaction with the enzyme and significantly affects the course of the crosslinking reaction and the properties of the resulting hydrogel.

In its first aspect the invention relates to the derivative based on hyaluronic acid according to the general formula (I)

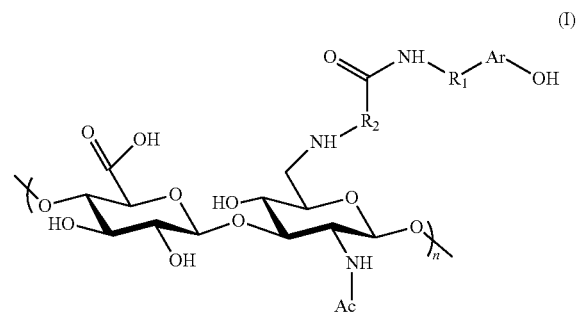

where Ar is phenyl and $R_1$ is ethylene, or Ar is indole and $R_1$ is ethylene, or Ar is indole and $R_1$ is karboxyethylene, and where $R_2$ is an alkyl having 3 to 7 carbons, and where n is within the range from 1 to 7500.

In another aspect, the invention relates to the method of preparation of the derivative according to the general formula (I), where first an aldehyde derivative of hyaluronic acid according to the formula (II) is prepared,

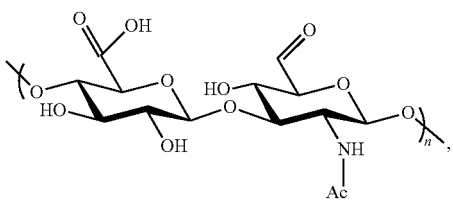

(II)

where the aldehyde derivative is prepared by using the oxidation system 4-acetamido-TEMPO/NaClO in a protic medium and has the substitution degree 5-15% and the molecular weight within the range 10000 g/mol to 2000000 g/mol, then separately the compound according to the general formula (III) is prepared

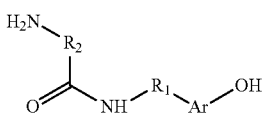

(III)

where Ar is phenyl and $R_1$ is ethylene, or Ar is indole and $R_1$ is ethylene, or Ar is indole and $R_1$ is karboxyethylene, and where $R_2$ is an alkyl having 3 to 7 carbons, and where n is within the range of 1 to 7500, wherein the compound according to the general formula (III) is prepared by a reaction of a spacer precursor according to the formula (IV)

Z—NH—R$_2$—COOH (IV), where Z is a protecting group which is commonly used for the protection of the primary amino group,
with the ligand according to the formula (V)

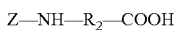

(V)

in an aprotic medium at a temperature within the range of 40° C. to 150° C. for 1 to 24 hours in the presence of an agent activating the carboxyl functional groups, forming the compound according to the general formula (VI)

Z—NH—R$_2$—CO—NH—R$_1$—Ar—OH (VI), from which the compound according to the general formula (III) is prepared by removing the protecting group Z, and then the aldehyde derivative of hyaluronic acid according to the formula (II) is reacted with the compound according to the general formula (III) at a pH within the range of 3 to 8 at room temperature for 1 to 72 hours in the presence of picoline-borane complex, forming the derivative according to the formula (I).

Therefore, the derivative according to the invention contains a ligand capable of undergoing oligomerization by means of a treatment by a suitable agent, and a flexible spacer which is inserted between the hyaluronan chain and the ligand. The ligand according to the general formula (V) according to the invention is preferably selected from the group comprising tyramine, serotonin and 5-hydroxytryptophane. The compound according to the general formula (IV), i.e. the spacer precursor, is preferably selected from the group of amino acids including derivatives of ω-[(tert butoxycarbonyl)amino]carboxylic acids where $R_2$ is an alkyl having 3 to 7 carbons.

In another preferred embodiment of the method according to the invention the reaction of the spacer precursor with the ligand takes place in THF or DMF at 50° C. for 2 to 6 hours in the presence of 1,1'-carbodiimidazole.

Further, it is preferred that the removal of the protecting group Z is performed by means of trifluoro acetic acid or hydrochloric acid.

Just for the sake of this invention, the intermediate spacer-ligand is represented by the compounds according to the general formula:

HO—Ar—R$_1$—NH—CO—R$_2$—NH$_2$

Preferably, the compound according to the general formula:

—CO—R$_2$—NH$_2$ where $R_2$ is an alkyl having 3 to 7, is used as a spacer.

The method of preparation of the derivative according to the invention may be characterized by the Scheme 1:

Scheme 1.: Example of a possible method of preparation of the derivative HA-spacer-ligand according to the invention

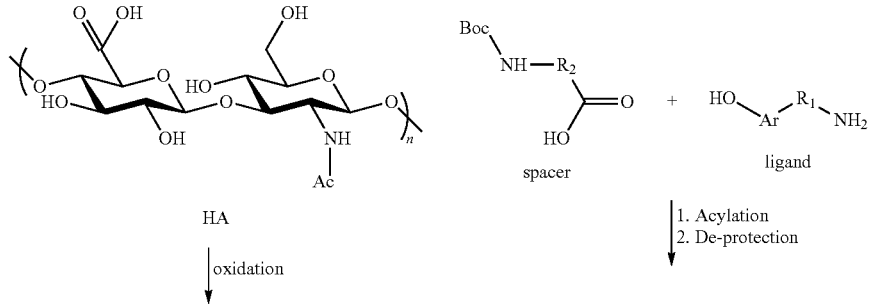

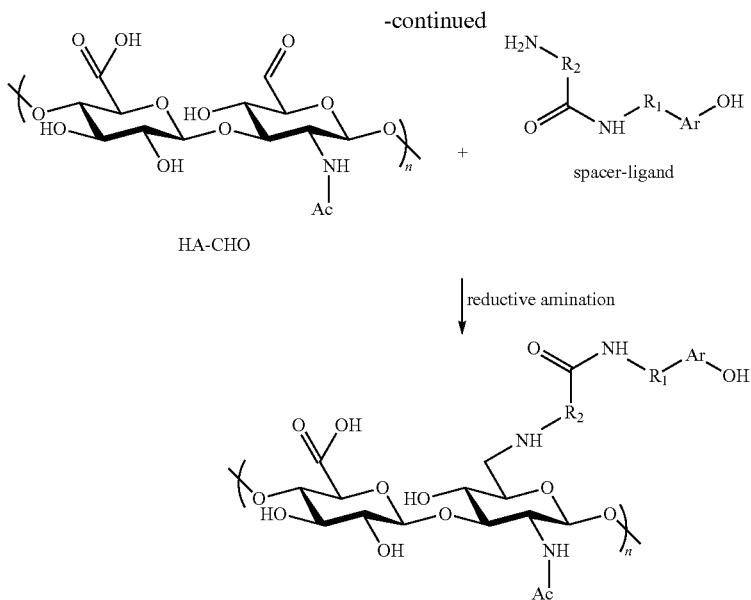

Further, the invention relates to the hydrogel formed by crosslinking the derivative according to the general formula (I) and a method of preparation thereof. This method of preparation of the hydrogel consists in that the derivative according to the general formula (I) is treated by a reactive phenoxy radicals generator, preferably by a system horseradish peroxidase and a source of hydroxyl radicals, which may be a solution of hydrogen peroxide in water, or a system oxidase-oxygen-substrate, e.g. galactose oxidase-galactose or glucose oxidase-glucose, at a pH within the range of 4 to 10.

Therefore, for oligomerization of reactive ligands, agents that are able to bring about the formation of phenoxy radicals from the aromatic rings of ligands are used. According to this invention, preferably the system peroxide/horseradish peroxidase is used. The peroxide may be introduced into the system in the form of a diluted solution, or is generated by a chemical reaction in situ. Hydrogen peroxide may be generated in the mixture by means of various kinds of enzymes (oxidases) from oxygen, as an electron acceptor, and a respective electron donor in an oxidation-reduction reaction. Preferably, a combination of galactose oxidase or glucose oxidase and the substrates thereof: galactose and glucose may be used. Other agents which are capable of causing the formation of phenoxy radicals in the presence of a molecular oxygen are enzymes tyrosinase, lactase etc.

The properties of these hydrogels are, as is generally known, affected by the chemical structure of the polymer and the concentration thereof, as well as the selected types of crosslinking agents and their amount used. The physically chemical properties of the polymer (HA derivative) are above all affected by the monomer structure, conformation of polymer chain segments, crosslinking degree and the molecular weight. The mechanical properties of the polymer are influenced by these as well. When the polymer is mechanically stressed, deformation thereof occurs wherein a part of the absorbed deformation energy dissipates—consumes for the change of the conformation of the network nodes and polymer chain segments and a part of the energy is irrevocably transformed to heat. The amount of the dissipated energy, and thus also the possibility of adopting various conformation arrangements within the polymer structure is associated with the stiffness of macromolecular chains and reflects the extent of elastic resistance of the material to deformation. Polymer materials composed of rigid inflexible chains and segments thereof then may exhibit a low extent of elastic resistance to deformation and fragility.

The increase of elasticity of these polymers is conducted according to the method of the invention where flexible segments are introduced into the polymer structure. Said segments are characterized by a higher freedom of individual molecules about their bonds whereby achieving an increase of possibilities of their conformational arrangement when subjected to the deformation energy, and of possibilities of dissipation of said energy. Therefore, an introduction of a suitable flexible spacer between the ligand and the basic hyaluronan chain leads to achieving a higher elasticity, tenacity and strength of the final material, which is very beneficial for e.g. hydrogels intended for scaffolds for treatment of defects of certain tissues exposed to higher loads, such as articular cartilage or bones. As described above, the introduction of the flexible spacer between the ligand and the basic hyaluronan chain may be preferably used also in case where the mechanical properties of the hydrogels depend on the concentration of the enzyme used as the crosslinking reaction catalyst. The introduction of the flexible spacer between the ligand and the basic hyaluronan chain provides for a sufficient steric accessibility of the reactive groups of the derivative for mutual dimerization, even after a partial crosslinking of the polymer.

This solution results in making the crosslinking reaction more effective which brings about a higher homogeneity of the prepared hydrogels and thus leads to overcoming the technology problems associated with crosslinking hyaluronan modified by hydroxyphenyl or heteroaryl phenol (tyramin, serotonin etc.) in the case where the crosslinking agents are horseradish peroxidase and hydrogen peroxide (or another type of phenoxy radicals generator).

However, surprisingly we have further found out that the introduction of our selected spacers between the ligand and the basic hyaluronan chain leads even at a very low substitution degree to a significant increase of the extent of elasticity, tenacity and strength of the final hydrogel based on said HA derivative.

Further, the invention relates to the use of hydrogels based on the derivatives according to the invention, especially in the field of tissue engineering, cosmetics, medicine and regenerative medicine. The use of the hydrogels described in this application is aimed especially at the basic material for formation of scaffolds in tissue engineering, mainly in the field of the treatment of articular and bone defects, such as coverings for wound healing, as a biodegradable barrier hindering from the formation of post-surgical coalescences, for augmentation of soft tissues and fillings of tissue defects and the like. When using the hydrogel as a material for scaffolds, the scaffolds may be either seeded or non-seeded. If they are seeded scaffolds, the type of the cells which are to be incorporated in the scaffold is selected depending on the aimed location of application.

BRIEF DESCRIPTION OF THE DRAWINGS

FIG. 1 represents deformation properties ("stress-strain" curves) obtained during the measurement of deformation of hydrogels based on the derivatives prepared according to Examples VIII, IX, XI and XII in compression.

PREFERRED EMBODIMENTS OF THE INVENTION

1. Example of the Synthesis of Derivatives

The synthesis of hyaluronan derivatives was conducted in several steps (see Scheme 1). The first step is the preparation of an aledehyde hyaluronan derivative (Example 1.7). Another step is the synthesis of various intermediates spacer-ligand (Examples 1.1 to 1.6) which were then linked to hyaluronan by the reductive amination process (Examples 1.9-1.14).

Examples also comprise the synthesis of hyaluronan derivatives in which the ligand (tyramine, hydroxytryptophane) is bound directly to the polysaccharide without using any spacer (Examples VIII). These derivatives and the hydrogels prepared therefrom served for comparing the properties thereof with the properties of the derivatives described in this application (derivatives HA-spacer-ligand—derivatives IX to XIV).

Example 1.1

Synthesis of 6-amino-N-[2-(4-hydroxyphenyl)ethyl] hexanamide (intermediate spacer-ligand (I))

6-[(tert-butoxycarbonyl)amino]hexane acid (1.00 g, 4.3 mmol) was dissolved in 50 ml of tetrahydrofuran (THF). To this solution of acid 1,1'-carbodiimidazol (0.70 g, 4.3 mmol) was added. The mixture was heated to 50° C. for sixty minutes. Then the reaction vessel was washed with an inert gas. To the reaction mixture tyramine (0.59 g, 4.3 mmol) was added. The mixture was further heated for another 2 hours. Then THF was removed by means of reduced pressure distillation. The evaporation residue was dissolved in 50 ml of ethylacetate. The solution was washed with 150 ml of purified water (divided into three parts). The organic layer was dried above a molecular sieve. Ethylacetate was removed by means of reduced pressure distillation. The evaporation residue was dissolved in 50 ml of MeOH and 2 ml of trifluoroacetic acid (TFA) were added. The solution was heated for 6 hours under reflux. The solvent was removed by reduced pressure distillation. The evaporation residue was dissolved in 50 ml of ethylacetate. The solution was washed with 150 ml of purified water (divided into three parts). The organic layer was dried above a molecular sieve. Ethylacetate was removed by reduced pressure distillation.

m=0.75 g (70% theory)

$^1$H NMR (D$_2$O, ppm) δ: 1.17 (m, 2 H, γ-CH$_2$-hexane acid); 1.48 (m, 2 H, β-CH$_2$-hexane acid); 1.58 (m, 2 H, δ-CH$_2$-hexane acid); 2.17 (t, 2 H, —CH$_2$—CO—); 2.73 (m, 2 H, —CH$_2$-Ph); 2.91 (m, 2 H, —CH$_2$—NH$_2$); 3.42 (m, 2 H, —CH$_2$—NH—CO—); 6.83 (d, 2 H, arom); 7.13 (d, 2 H, arom).

$^{13}$C NMR (D$_2$O, ppm) δ: 24 (γ-C-hexane acid); 26 (δ-C-hexane acid); 33 (β-C-hexane acid); 35 (—C—CO—); 39 (—C—NH$_2$); 40 (C-Ph); 63 (—C—NH—CO—); 115 (C3 arom); 126 (C1 arom); 130 (C2 arom.); 153 (C4 arom); 176 (—CO—).

Example 1.2

Synthesis of 4-amino-N-[2-(4-hydroxyphenyl)ethyl] butanamide (intermediate spacer-ligand (II))

4-[(tert-butoxycarbonyl)amino]butane acid (0.50 g, 2.5 mmol) was dissolved in 25 ml of tetrahydrofuran (THF). To the solution of acid 1,1'-carbodiimidazole (0.40 g, 25 mmol) was added. The mixture was heated to 50° C. for sixty minutes. Then the reaction vessel was washed with an inert gas. To the reaction mixture tyramine (0.34 g, 25 mmol) was added. The mixture was further heated for another 2 hours. Then THF was removed by reduced pressure distillation. The evaporation residue was dissolved in 50 ml of ethylacetate. The solution was washed with 150 ml of purified water (divided into three parts). The organic layer was dried above a molecular sieve. Ethylacetate was removed by means of reduced pressure distillation. The evaporation residue was dissolved in 50 ml of MeOH and 2 ml of trifluoroacetic acid were added. The solution was heated for 6 hours under reflux. The solvent was removed by reduced pressure distillation. The evaporation residue was dissolved in 50 ml of ethylacetate. The solution was washed with 150 ml of purified water (divided into three parts). The organic layer was dried above a molecular sieve. Ethylacetate was removed by means of reduced pressure distillation.

m=0.44 g (80% theory)

$^1$H NMR (D$_2$O, ppm) δ: 1.75 (m, 2 H, β-CH$_2$-butane acid); 2.16 (t, 2 H, —CH$_2$—CO—); 2.59 (m, 2 H, —CH$_2$—In); 2.78 (m, 2 H, —CH$_2$—NH$_2$); 3.20 (m, 2 H, —CH$_2$—NH—CO—); 6.69 (d, 2 H, arom); 6.99 (d, 2 H, arom).

$^{13}$C NMR (D$_2$O, ppm) δ: 23 (β-C-butane acid); 25 (t, 2 H, —C—CO—); 32 (—C—NH$_2$); 45 (CH$_2$—Ar); 60 (—C—NH—CO—); 115 (C3 arom); 117 (C1 arom); 129 (C2 arom.); 155 (C4 arom); 171 (—CO—).

Example 1.3

Synthesis of 8-amino-N-[2-(4-hydroxyphenyl)ethyl] octanamide (intermediate spacer-ligand (III))

8-[(tert-butoxycarbonyl)amino]octane acid (0.50 g, 1.9 mmol) was dissolved in 25 ml of tetrahydrofuran (THF). To the solution of acid 1,1'-carbodiimidazole (0.31 g, 1.9 mmol) was added. The mixture was heated to 50° C. for sixty minutes. Then the reaction vessel was washed with an inert gas. To the reaction mixture tyramine (0.26 g, 1.9 mmol) was added. The mixture was further heated for another 2 hours. Then THF was removed by reduced pressure distillation. The evaporation residue was dissolved in 50 ml of ethylacetate. The solution was washed with 150 ml of purified water (divided into three parts). The organic layer was dried above a molecular sieve. Ethylacetate was removed by means of reduced pressure distillation. The evaporation residue was dissolved in 50 ml of MeOH and 2 ml of trifluoroacetic acid were added. The solution was heated for 6 hours under reflux. The solvent was removed by reduced pressure distillation. The evaporation residue was dissolved in 50 ml of ethylacetate. The solution was washed with 150 ml of purified water (divided into three parts). The organic layer was dried above a molecular sieve. Ethylacetate was removed by means of reduced pressure distillation.

m=0.40 g (75% theory)

$^1$H NMR (CDCl$_3$, ppm) δ: 1.16-1.34 (m, 6 H, C4 až C6-CH$_2$-octane acid); 1.56-1.44 (m, 4 H, C3 a C7 octane acid); 2.58 (m, 2 H, —CH$_2$—Ar); 2.78 (m, 2 H, —CH$_2$—NH$_2$); 3.19 (m, 2 H, —CH$_2$—NH—CO—); 6.68 (d, 2 H, arom); 6.98 (d, 2 H, arom).

$^{13}$C NMR (CDCl$_3$, ppm) δ: 21 (C7 octane acid); 24 (C4 octane acid); 26 (C6-octane acid); 28 (C5-octane acid); 33 (C3-octane acid); 35 (—C—CO—); 39 (—C—NH$_2$); 40 (C-Ph); 63 (—C—NH—CO—); 115 (C3 arom); 126 (C1 arom); 130 (C2 arom.); 153 (C4 arom); 176 (—CO—).

Example 1.4

Synthesis of 4-amino-N-[2-(5-hydroxy-1H-indol-3-yl)ethyl]butanamide (intermediate spacer-ligand (IV))

4-[(tert-butoxycarbonyl)amino]butane acid (0.50 g, 2.5 mmol) was dissolved in 25 ml of N,N-dimethylformamid (DMF). To the solution of acid 1,1'-carbodiimidazole (0.40 g, 2.5 mmol) was added. The mixture was heated to 50° C. for sixty minutes. Then the reaction vessel was washed with an inert gas. To the reaction mixture a solution of 5-hydroxytryptamine hydrochloride (0.52 g, 2.5 mmol) and triethylamine (0.68 ml; 4.9 mmol) in 25 ml of DMF was added. The mixture was further heated for another 2 hours. The mixture was diluted by adding ethylacetate (100 ml). The resulting solution was washed with 300 ml of purified water (divided into three parts). The organic layer was dried above a molecular sieve. Ethylacetate was removed by means of reduced pressure distillation. The evaporation residue was dissolved in 50 ml of MeOH and 2 ml of trifluoroacetic acid were added. The solution was heated for 6 hours under reflux. The solvent was removed by reduced pressure distillation. The evaporation residue was dissolved in 50 ml of ethylacetate. The solution was washed with 150 ml of purified water (divided into three parts). The organic layer was dried above a molecular sieve. Ethylacetate was removed by means of reduced pressure distillation.

m=0.43 g (65% theory)

$^1$H NMR: (DMSO, ppm) δ: 1.77 (m, 2 H, β-CH$_2$-butane acid); 2.20 (t, 2 H, —CH$_2$—CO—); 2.73 (m, 2 H, —CH$_2$—In); 2.81 (m, 2 H, —CH$_2$—NH$_2$); 3.30 (m, 2 H, —CH$_2$—NH—CO—); 6.60 (d, 1 H, C6-arom); 6.82 (s, 1 H, C4-arom); 7.03 (s, 1 H, C2-arom); 7.13 (d, 1 H, C7-arom).

$^{13}$C NMR (DMSO, ppm) δ: 23 (β-C-butane acid); 25 (t, 2 H, —C—CO—); 32 (—C—NH$_2$); 39 (CH$_2$—In); 60 (—C—NH—CO—); 102 (C4 arom); 110 (C6 arom); 111 (C7 arom.); 111 (C3 arom.); 123 (C2 arom); 127 (C7-C—NH— arom); 131 (C4-C—C3-arom); 150 (C5 arom); 171 (—CO—).

Example 1.5

Synthesis of 6-amino-N-[2-(5-hydroxy-1H-indol-3-yl)ethyl]hexanamide (intermediate spacer-ligand (V))

6-[(tert-butoxycarbonyl)amino]hexane acid (1.00 g, 4.3 mmol) was dissolved in 50 ml of N,N-dimethylformamid (DMF). To the solution of acid 1,1'-carbodiimidazol (0.70 g, 4.3 mmol) was added. The mixture was heated to 50° C. for sixty minutes. Then the reaction vessel was washed with an inert gas. To the reaction mixture a solution of 5-hydroxytryptamine hydrochloride (0.91 g, 4.3 mmol) and triethylamine (0.68 ml, 49 mmol) in 25 ml of DMF was added. The mixture was further heated for another 2 hours. The mixture was diluted by adding ethylacetate (100 ml). The resulting solution was washed with 300 ml of purified water (divided into three parts). The organic layer was dried above a molecular sieve. Ethylacetate was removed by means of reduced pressure distillation. The evaporation residue was dissolved in 50 ml of MeOH and 2 ml of trifluoroacetic acid were added. The solution was heated for 6 hours under reflux. The solvent was removed by reduced pressure distillation. The evaporation residue was dissolved in 50 ml of ethylacetate. The solution was washed with 150 ml of purified water (divided into three parts). The organic layer was dried above a molecular sieve. Ethylacetate was removed by means of reduced pressure distillation.

m=0.75 g (60% theory)

$^1$H NMR: (DMSO, ppm) δ: 1.17 (m, 2 H, γ-CH$_2$-hexane acid); 1.48 (m, 2 H, β-CH$_2$-hexane acid); 1.58 (m, 2 H, 8-CH$_2$-hexane acid); 2.17 (t, 2 H, —CH$_2$—CO—); 2.73 (m, 2 H, —CH$_2$—In); 2.91 (m, 2 H, —CH$_2$—NH$_2$); 3.42 (m, 2 H, —CH$_2$—NH—CO—); 6.60 (d, 1 H, C6-arom); 6.82 (s, 1 H, C4-arom); 7.03 (s, 1 H, C2-arom); 7.13 (d, 1 H, C7-arom).

$^{13}$C NMR (DMSO, ppm) δ: 24 (γ-C-hexane acid); 26 (δ-C-hexane acid); 33 (β-C-hexane acid); 35 (—C—CO—); 39 (—C—NH$_2$); 40 (C—In); 63 (—C—NH—CO—); 102 (C4 arom); 110 (C6 arom); 111 (C7 arom.); 111 (C3 arom.); 123 (C2 arom); 127 (C7-C—NH— arom); 131 (C4-C—C3-arom); 150 (C5 arom); 171 (—CO—).

Example 1.6

Preparation of 2-[(6-aminohexanoyl)amino]-3-(5-hydroxy-1H-indol-3-yl)-propane acid (intermediate spacer-ligand VI)

6-[(tert-butoxycarbonyl)amino]hexane acid (0.50 g, 2.2 mmol) was dissolved in 50 ml of tetrahydrofurane (THF). To the solution of acid 1,1'-carbodiimidazole (0.35 g, 2.2 mmol) was added. The mixture was heated to 50° C. for sixty minutes. Then the reaction vessel was washed with an inert gas. To the reaction mixture 5-hydroxytryptophane (0.48 g, 2.2 mmol) was added. The mixture was further heated for another 2 hours. The mixture was diluted by adding ethylacetate (100 ml). The resulting solution was washed with 300 ml of purified water (divided into three parts). The organic layer was dried above a molecular sieve. Ethylacetate was removed by reduced pressure distillation. The evaporation residue was dissolved in 50 ml of MeOH and 2 ml of trifluoroacetic acid were added. The solution was heated for 6 hours under reflux. The solvent was removed by reduced pressure distillation. The evaporation residue was dissolved in 50 ml of ethylacetate. The solution was washed with 150 ml of purified water (divided into three parts). The organic layer was dried above a molecular sieve. Ethylacetate was removed by means of reduced pressure distillation.

m=0.62 g (85% theory)

$^1$H NMR: (DMSO, ppm) δ: 1.17 (m, 2 H, γ-CH$_2$-hexane acid); 1.48 (m, 2 H, (3-CH$_2$-hexane acid); 1.58 (m, 2 H, 8-CH$_2$-hexane acid); 2.19 (t, 2 H, —CH$_2$—CO—); 2.51 (m, 2 H, —CH$_2$—In); 2.90 (m, 2 H, —CH$_2$—NH$_2$); 3.81 (m, 2 H, —CH$_2$—NH—CO—); (m, 2 H, —CH$_2$—NH—CO—);

6.61 (d, 1 H, C6-arom); 6.95 (s, 1 H, C4-arom); 7.02 (s, 1 H, C2-arom); 7.13 (d, 1 H, C7-arom).

$^{13}$C NMR (DMSO, ppm) δ: 24 (γ-C-hexane acid); 26 (δ-C-hexane acid); 33 (β-C-hexane acid); 35 (—C—CO—); 39 (—C—NH$_2$); 40 (C-Ph); 55 (—C—NH—CO—); 102 (C4 arom); 110 (C6 arom); 111 (C7 arom.); 111 (C3 arom.); 123 (C2 arom); 127 (C7-C—NH— arom); 131 (C4-C—C3-arom); 150 (C5 arom); 171 (—CO—).

Example 1.7

Preparation of Aldehyde Derivative (HA-CHO)—General Procedure (VII)

Hylauronan (10.00 g, $M_w$=2 MDa) was dissolved in 750 ml of 2.5% (w/w) solution of Na$_2$HPO$_4$. 12 H$_2$O. The solution was cooled to 5° C. To the resulting solution 2.60 g of NaBr and 0.05 g of 4-acetamido-2,2,6,6-tetramethylpiperidine-1-oxyl were added. After a thorough homogenization of the solution, 3 ml of the solution of NaClO (10-15% of available Cl$_2$) were added to the reaction mixture. The reaction proceeded while continually stirring for 15 min. The reaction was quenched by an addition of 100 ml of 40% solution of propan-2-ol. The product was purified by ultrafiltration and isolated by means of precipitation by propan-2-ol.

IR (KBr): 3417, 2886, 2152, 1659, 1620, 1550, 1412, 1378, 1323, 1236, 1204, 1154, 1078, 1038, 945, 893 cm$^{-1}$.

$^1$H NMR (D$_2$O) δ: 2.01 (s, 3 H, CH$_3$—), 3.37-3.93 (m, hyaluronan body), 4.46 (s, 1H, anomer), 4.54 (s, 1H anomer, —O—CH(OH)—), 5.27 (geminal glycol —CH—(OH)$_2$).

Example 1.8

Synthesis of Tyramine Derivative (VIII)

Aldehyde HA derivative (VII) (5.00 g) was dissolved in 500 ml of demineralized water. The pH of the solution was adjusted to 3 by means of acetic acid. Then tyramine in the form of a solution in 100 ml of 40% propan-2-ol was added to the reaction mixture (1.70 g). The mixture was further stirred for 1 hour at room temperature; Then a solution of picoline-borane complex (0.50 g) in 50 ml of 40% propan-2-ol was added to the mixture. The reaction mixture was further stirred for 12 hours at room temperature. The low-molecular ballast substances were removed from the product by means of ultrafiltration. The product was obtained by means of precipitation by propan-2-ol. The precipitate was deprived of humidity and residual propan-2-ol by drying in a hot-air drier (40° C., 3 days).

IR (KBr): 3400, 2893, 2148, 1660, 1620, 1549, 1412, 1378, 1323, 1236, 1204, 1154, 1078, 1038, 945, 893 cm$^{-1}$.

$^1$H NMR (D$_2$O) δ: 2.01 (s, 3 H, CH$_3$—), 2.66-2.77 (m, 4 H, —CH$_2$—CH$_2$—NH—), 3.00 (s, 1H, H—CH—NH—), 3.37-3.93 (m, hyaluronan body), 4.46 (s, 1H, anomer), 4.54 (s, 1H anomer., —O—CH(OH)—), 6.59 (d, 2H, arom.), 7.04 (d, 2H. arom).

Example 1.9

Preparation of Tyramine HA Derivative with a C$_6$ Spacer (IX)

Aldehyde HA derivative (VII) (5.00 g) was dissolved in 500 ml of demineralized water. The pH of the solution was adjusted to 3 by means of acetic acid. Then 6-amino-N-[2-(4-hydroxyphenyl)ethyl]hexanamide (intermediate (I)) (0.625 g, 2.5 mmol) was added to the solution of HA-CHO. The mixture was stirred for 2 hours at room temperature. Then the complex of picoline-borane (0.270 g, 2.5 mmol) was added to the reaction mixture. The mixture was stirred for further 12 hours at room temperature. The product was purified by means of ultrafiltration and isolated from the retentate by means of precipitation by propan-2-ol. The precipitate was deprived of humidity and residual propan-2-ol by drying in a hot-air drier (40° C., 3 days).

IR (KBr): 3425, 2893, 2148, 1660, 1620, 1549, 1412, 1378, 1323, 1236, 1204, 1154, 1078, 1038, 945, 893 cm$^{-1}$.

$^1$H NMR (D$_2$O) δ: 1.25 (t, 2 H, γ-CH$_2$-aminohexane acid), 1.48 (m, 2 H, δ-CH$_2$-aminohexane acid) 1.51 (m, 2 H, β-CH$_2$-aminohexane acid), 2.01 (s, 3 H, CH$_3$—), 2.65 (m, 2H, Ph-CH$_2$—), 2.73 (m, 2H, ε-CH$_2$-aminohexane acid), 3.37-3.93 (m, hyaluronan body), 4.46 (s, 1H, anomer), 4.54 (s, 1H anomer., —O—CH(OH)—), 6.59 (d, 2H, arom.), 7.01 (d, 2H. arom).

Example 1.10

Preparation of HA Derivative with a C$_4$ Spacer and 5-Hydroxy Tryptamine (X)

Aldehyde HA derivative (VII) (3.00 g) a Na$_2$HPO$_4$. 12 H$_2$O (7.50 g) was dissolved in 300 ml of demineralized water. Then 4-amino-N-[2-(5-hydroxy-1H-indol-3-yl)ethyl] butane amide (0.40 g, 1.5 mmol)—(intermediate (IV)) was added to the solution of HA-CHO. The mixture was stirred for 2 hours at room temperature. Then the complex of picoline-borane (0.16 g, 1.5 mmol) was added to the reaction mixture. The mixture was stirred for further 12 hours at room temperature. The product was purified by ultrafiltration and isolated from the retentate by means of precipitation by propan-2-ol. The precipitate was deprived of humidity and residual propan-2-ol by drying in a hot-air drier (40° C., 3 days).

IR (KBr): 3400, 2893, 2148, 1660, 1620, 1549, 1412, 1378, 1323, 1236, 1204, 1154, 1078, 1038, 945, 893 cm$^{-1}$.

$^1$H NMR (D$_2$O) δ: 1.73 (m, 2 H, β-CH$_2$-aminobutane acid), 2.01 (s, 3 H, CH$_3$), 2.60 (m, 2H, γ-CH$_2$-aminobutane acid), 2.93 (m, 2H, Ind-CH$_2$—), 3.37-3.93 (m, hyaluronan body), 4.46 (s, 1H, anomer), 4.54 (s, 1H anomer., —O—CH (OH)—), 6.85 (d, 1H, arom.), 7.09 (s, 1H. arom), 7.21 (s, 1H. arom), 7.40 (s, 1H. arom).

Example 1.11

Preparation of Tyraminated HA Derivative with a C$_4$ Spacer (XI)

Aldehyde HA derivative (VII) (3.50 g) was dissolved in 350 ml of demineralized water. The pH of the solution was adjusted to 3 by means of acetic acid. Then 4-amino-N-[2-(4-hydroxyphenyl)ethyl]butane amide (0.40 g, 1.8 mmol)—(intermediate (II)) was added to the solution of HA-CHO. The mixture was stirred for 2 hours at room temperature. Then the complex of picoline-borane (0.19 g, 1.8 mmol) was added to the reaction mixture. The mixture was stirred for further 12 hours at room temperature. The product was purified by means of ultrafiltration and isolated from the retentate by means of precipitation by propan-2-ol. The precipitate was deprived of humidity and residual propan-2-ol by drying in a hot-air drier (40° C., 3 days).

IR (KBr): 3425, 2893, 2148, 1660, 1620, 1549, 1412, 1378, 1323, 1236, 1204, 1154, 1078, 1038, 945, 893 cm$^{-1}$.

$^1$H NMR (D$_2$O) δ: 1.25 (t, 2 H, γ-CH$_2$-aminohexane acid), 1.48 (m, 2 H, δ-CH$_2$-aminohexane acid) 1.51 (m, 2 H, β-CH$_2$-aminohexane acid), 2.01 (s, 3 H, CH$_3$—), 2.65 (m, 2H, Ph-CH$_2$—), 2.73 (m, 2H, ϵ-CH$_2$-aminohexane acid), 3.37-3.93 (m, hyaluronan body), 4.46 (s, 1H, anomer), 4.54 (s, 1H anomer., —O—CH(OH)—), 6.59 (d, 2H, arom.), 7.01 (d, 2H. arom).

Example 1.12

Preparation of Tyraminated HA Derivative with a C$_8$ Spacer (XII)

Aldehyde HA derivative (VII) (2.90 g) was dissolved in 300 ml of demineralized water. The pH of the solution was adjusted to 3 by means of acetic acid. Then 8-amino-N-[2-(4-hydroxyphenyl)ethyl]octane amide (0.40 g, 1.4 mmol)—(intermediate (III)) was added to the solution of HA-CHO. The mixture was stirred for 2 hours at room temperature. Then the complex of picoline-borane (0.15 g, 1.4 mmol) was added to the reaction mixture. The mixture was stirred for further 12 hours at room temperature. The product was purified by means of ultrafiltration and isolated from the retentate by means of precipitation by propan-2-ol. The precipitate was deprived of humidity and residual propan-2-ol by drying in a hot-air drier (40° C., 3 days).
IR (KBr): 3425, 2893, 2148, 1660, 1620, 1549, 1412, 1378, 1323, 1236, 1204, 1154, 1078, 1038, 945, 893 cm$^{-1}$.
$^1$H NMR (D$_2$O) δ: 1.16-1.34 (m, 6 H, C4 až C6-CH$_2$-octane acid); 1.56-1.44 (m, 4 H, C3 a C7 octane acid); 2.01 (s, 3 H, CH$_3$—), 2.58 (m, 2 H, —CH$_2$—Ar); 2.78 (m, 2H, —CH$_2$—NH—), 3.37-3.93 (m, hyaluronan body), 4.46 (s, 1H, anomer), 4.54 (s, 1H anomer., —O—CH(OH)—), 6.59 (d, 2H, arom.), 7.01 (d, 2H. arom).

Example 1.13

Preparation of HA Derivative with a C$_6$ Spacer and 5-Hydroxy Tryptamine (XIII)

Aldehyde HA derivative (VII) (5.00 g) and Na$_2$HPO$_4$. 12 H$_2$O (12.5 g) were dissolved in 500 ml of demineralized water. Then 6-amino-N-[2-(5-hydroxy-1H-indol-3-yl)ethyl] hexane amide (0.73 g, 2.5 mmol)—(intermediate (V)) was added to the solution of HA-CHO. The mixture was stirred for 2 hours at room temperature. Then the complex of picoline-borane (0.27 g, 2.5 mmol) was added to the reaction mixture. The mixture was stirred for further 12 hours at room temperature. The product was purified by means of ultrafiltration and isolated from the retentate by means of precipitation by propan-2-ol. The precipitate was deprived of humidity and residual propan-2-ol by drying in a hot-air drier (40° C., 3 days).
IR (KBr): 3400, 2893, 2148, 1660, 1620, 1549, 1412, 1378, 1323, 1236, 1204, 1154, 1078, 1038, 945, 893 cm$^{-1}$.
$^1$H NMR (D$_2$O) δ: 1.25 (t, 2 H, γ-CH$_2$-aminohexane acid), 1.48 (m, 2 H, δ-CH$_2$-aminohexane acid) 1.51 (m, 2 H, β-CH$_2$-aminohexane acid), 2.01 (s, 3 H, CH$_3$—), 2.65 (m, 2H, Ph-CH$_2$—), 2.73 (m, 2H, ϵ-CH$_2$-aminohexane acid), 3.37-3.93 (m, hyaluronan body), 4.46 (s, 1H, anomer), 4.54 (s, 1H anomer., —O—CH(OH)—), 6.85 (d, 1H, arom.), 7.09 (s, 1H. arom), 7.21 (s, 1H. arom), 7.40 (s, 1H. arom).

Example 1.14

Preparation of HA Derivative with a C$_6$ Spacer and 5-Hydroxy Tryptophane (XIV)

Aldehyde HA derivative (VII) (3.50 g) and Na$_2$HPO$_4$. 12 H$_2$O (8.75 g) was dissolved in 350 ml of demineralized water. Then 2-[(6-aminohexanoyl)amino]-3-(5-hydroxy-1H-indole-3-yl)propan acid (0.60 g, 1.8 mmol)—(intermediate (VI)) was added to the HA-CHO solution. The mixture was mixed for 2 hours at room temperature. Then the complex of picoline-borane (0.19 g, 1.8 mmol) was added to the reaction mixture. The mixture was stirred for further 12 hours at room temperature. The product was purified by ultrafiltration and isolated from the retentate by means of precipitation by propan-2-ol. The precipitate was deprived of humidity and residual propan-2-ol by drying in a hot-air drier (40° C., 3 days).
IR (KBr):: 3400, 2893, 2148, 1660, 1620, 1549, 1412, 1378, 1323, 1236, 1204, 1154, 1078, 1038, 945, 893 cm$^{-1}$.
$^1$H NMR (D$_2$O) δ: 1.25 (t, 2 H, γ-CH$_2$-aminohexane acid), 1.48 (m, 2 H, δ-CH$_2$-aminohexane acid) 1.51 (m, 2 H, β-CH$_2$-aminohexane acid), 2.01 (s, 3 H, CH$_3$—), 2.65 (m, 2H, Ph-CH$_2$—), 2.73 (m, 2H, ϵ-CH$_2$-aminohexane acid), 3.37-3.93 (m, hyaluronan body), 4.46 (s, 1H, anomer), 4.54 (s, 1H anomer., —O—CH(OH)—), 6.85 (d, 1H, arom.), 7.09 (s, 1H. arom), 7.21 (s, 1H. arom), 7.40 (s, 1H. arom).

Example 1.15

General Procedure of the Preparation of the Hydrogel Based on HA Derivative with a Spacer and 5-Hydroxytryptophan and Based on a Tyramine Derivative The selected HA derivative is dissolved in 0.1 M PBS pH 7.4. The amount of the derivative is chosen according to the desired concentration. To the solution of the derivative, the desired amount of the enzyme is added. After a thorough homogenization a diluted hydrogen peroxide solution is added. The mixture is homogenized again and a transparent gel is formed.

Example 1.16

Preparation of the Hydrogel Based on Tyramine Derivative 40 to 60 mg (according to the desired concentration of the polymer solution) of the HA derivative HA prepared according to the example 1.8 (VIII) is dissolved in 2 ml of 0.1 M PBS having pH 7.4. Then 20 ul of the solution of the enzyme HRP (24 mg of the enzyme HRP dissolved in 1 ml of 0.1M PBS o pH 7.4) were added to the solution of the derivative. After a thorough homogenization 100 μl of the solution of H$_2$O$_2$ (33 μl 30% H$_2$O$_2$ dissolved in 10 ml of 0.1 M PBS having pH 7.4) were added. The mixture is homogenized and a transparent gel is formed.

Example 1.17

Preparation of the Hydrogel Based on the Tyramine HA Derivative with a Spacer 40-60 mg (according to the desired concentration of the polymer solution) of the HA derivative prepared according to the example 1.9 (IX), 1.11 (XI) or 1.12 (XII) is dissolved in 2 ml of 0.1 M PBS having pH 7.4. To the solution of the derivative, 10 ul of the solution of the enzyme HRP (2.4 mg of the enzyme HRP dissolved in 1 ml of 0.1 M PBS having pH 7.4) were added. After a thorough homogenization 100 μl of the solution of H$_2$O$_2$ (33 μl of 30% H$_2$O$_2$ dissolved in 10 ml of 0.1 M PBS having pH 7.4) were added. The mixture is homogenized and a transparent gel is formed.

2. Differences in the Hydrogel Properties

Example 2.1

Difference in Mechanical Properties of Hydrogels Depending on the Type of HA Derivative Used and the Amount of the Added Enzyme Samples of hydrogels from the derivatives VIII (tyramine, without the incorporated spacer), IX, XI and XII (with an incorporated spacer) were prepared according to the examples 1.16 or 1.17, depending on the type of the derivative used. The samples were, after a thorough homogenization, let mature for 120 minutes at room temperature. The analogues of the derivatives used for the preparation of the compared hydrogels always had a comparable molecular weight and substitution degree. All samples had the same dimensions and were tested at constant laboratory conditions (temperature, pressure, humidity).

Young modulus of elasticity in compression, tenacity, compression strength and the corresponding sample deformation were measured for each sample; and for viscoelastic properties of the samples the shear modulus and loss angle were measured.

The obtained data clearly imply that the introduction of the flexible spacer between the ligand and basic hyaluronan chain leads to a higher elasticity, tenacity and strength of the hydrogels based on said derivatives, compared to the hydrogels based on analogous hyaluronan derivatives without any spacer.

Table 1 shows the comparison of the mechanical properties of the hydrogel depending on the type of derivative used for the preparation thereof. The concentration (%) means the concentration of the polymer in the solution from which the hydrogel was prepared, the substitution degree (%) indicates the substitution degree by the reactive/crosslinking ligand, i.e. the number of the bound ligands per 100 of the structural units of the polymer, wherein in case of HA the structural unit of the polymer is disaccharide (or dimer) glycosamine+ glucuronic acid.

TABLE 1

| | Type of the derivative used | | | | |
|---|---|---|---|---|---|
| | HA derivative according to the example VIII | HA derivative according to the example IX | HA derivative according to the example VIII | HA derivative according to the example XI | HA derivative according to the example XII |
| Mw (kDa)/ concentration (%) | 320/3 | 250/3 | 280/2 | 280/2 | 285/2 |
| Substitution degree (%) | 3 | 3 | 2 | 1 | 1 |
| Youngův modulus of elasticity in compression (kPa) | 6.59 | 5.68 | 8.99 | 3.87 | 8.19 |
| Compression strength (kPa) | 73 | 310 | 108 | 167 | 218 |
| Deformation in compression strength (%) | 67 | 68 | 58 | 65 | 65 |
| Tenacity (J/m$^3$) | 9150 | 23460 | 8050 | 9670 | 13650 |
| Loss angle (°) | 0.12 | 0.18 | 0.19 | 0.96 | 0.43 |
| Shear modulus (Pa) | 1861 | 1534 | 876 | 504 | 1105 |

1. Slaughter, B. V.; Khurshid, S. S.; Fisher, O. Z.; Khademhosseini, A.; Peppas, N. A., Hydrogels in Regenerative Medicine. *Advanced Materials* 2009, 21 (32-33), 3307-3329.
2. Benedetti, L.; Cortivo, R.; Berti, T.; Berti, A.; Pea, F.; Mazzo, M.; Moras, M.; Abatangelo, G., Biocompatibility and biodegradation of different hyaluronan derivatives (Hyaff) implanted in rats. *Biomaterials* 1993, 14 (15), 1154-1160.
3. Calabro, A.; Gross, R. A.; Darr, A. B. Hydroxyphenyl cross-linked macromolecular network and applications thereof. 2004.
4. Calabro, A.; Akst, L.; Alam, D.; Chan, J.; Darr, A. B.; Fukamachi, K.; Gross, R. A.; Haynes, D.; Kamohara, K.; Knott, D. P.; Lewis, H.; Melamud, A.; Miniaci, A.; Strome, M. Hydroxyphenyl cross-linked macromolecular network and applications thereof. 2008 (WO2006/010066).
5. Tan, H.; Chu, C. R.; Payne, K. A.; Marra, K. G., Injectable in situ forming biodegradable chitosan-hyaluronic acid based hydrogels for cartilage tissue engineering. *Biomaterials* 2009, 30 (13), 2499-2506.
6. Dan, A.; Calabro, A., Synthesis and characterization of tyramine-based hyaluronan hydrogels. *Journal of Materials Science: Materials in Medicine* 2009, 20 (1), 33-44.
7. Kurisawa, M.; Lee, F.; Chung, J. E. Formation of Hydrogel in the Presence of Peroxidase and Low Concentration of Hydrogen Peroxide 2009 (WO2009/148405).
8. Lee, F.; Chung, J. E.; Kurisawa, M., An injectable enzymatically crosslinked hyaluronic acid-tyramine hydrogel system with independent tuning of mechanical strength and gelation rate. *Soft Matter* 2008, 4, 880-887.
9. Akkara, J. A.; Senecal, K. J.; Kaplan, D. L., Synthesis and characterization of polymers produced by horseradish peroxidase in dioxane. *Journal of Polymer Science Part A: Polymer Chemistry* 1991, 29 (11), 1561-1574.
10. Shutava, T.; Zheng, Z.; John, V.; Lvov, Y., Microcapsule modification with peroxidase-catalyzed phenol polymerization. *Biomacromolecules* 2004, 5 (3), 914-21.
11. Ghan, R.; Shutava, T.; Patel, A.; John, V. T.; Lvov, Y., Enzyme-Catalyzed Polymerization of Phenols within Polyelectrolyte Microcapsules. *Macromolecules* 2004, 37 (12), 4519-4524.
12. Higashimura, H.; Kobayashi, S., *Oxidative Polymerization*. John Wiley & Sons, Inc.: 2002.
13. Veitch, N. C., Horseradish peroxidase: a modern view of a classic enzyme. *Phytochemistry* 2004, 65 (3), 249-259.
14. Gilabert, M. A.; Phenoll, L. G.; Garcia-Molina, F.; Garcia-Ruiz, P. A.; Tudela, J.; Garcia-Canovas, F.; Rodri guez-Lopez, J. N., Stereospecificity of horseradish peroxidase. *Biol Chem* 2004, 385 (12), 1177-84.
15. Uyama, H.; Kobayashi, S., Enzymatic Synthesis of Polyphenols. *Current Organic Chemistry* 2003, 7, 1387.
16. Gilabert, M. A.; Phenoll, L. G.; Garcia-Molina, F.; Tudela, J.; Garcia-Canovas, F.; Rodriguez-Lopez, J. N., Kinetic characterization of phenol and aniline derivates as substrates of peroxidase. *Biol Chem* 2004, 385 (9), 795-800.
17. Gilabert, M. A.; Hiner, A. N.; Garcia-Ruiz, P. A.; Tudela, J.; Garcia-Molina, F.; Acosta, M.; Garcia-Canovas, F.; Rodriguez-Lopez, J. N., Differential substrate behaviour of phenol and aniline derivatives during oxidation by horseradish peroxidase: kinetic evidence for a two-step mechanism. *Biochim Biophys Acta* 2004, 1699 (1-2), 235-43.
18. Hewson, W. D.; Dunford, H. B., Oxidation of p-cresol by horseradish peroxidase compound I. *J Biol Chem* 1976, 251 (19), 6036-42.
19. Burner, U.; Obinger, C., Transient-state and steady-state kinetics of the oxidation of aliphatic and aromatic thiols by horseradish peroxidase. *FEBS Letters* 1997, 411 (2-3), 269-274.
20. Patel, P. K.; Mondal, M. S.; Modi, S.; Behere, D. V., Kinetic studies on the oxidation of phenols by the horseradish peroxidase compound II. *Biochim Biophys Acta* 1997, 1339 (1), 79-87.
21. Hewson, W. D.; Dunford, H. B., Stoichiometry of the reaction between horseradish peroxidase and p-cresol. *J Biol Chem* 1976, 251 (19), 6043-52.
22. Job, D.; Dunford, H. B., Substituent effect on the oxidation of phenols and aromatic amines by horseradish peroxidase compound I. *Eur J Biochem* 1976, 66 (3), 607-14.
23. Dunford, H. B.; Cotton, M. L., Kinetics of the oxidation of p-aminobenzoic acid catalyzed by horseradish peroxidase compounds I and II. *J Biol Chem* 1975, 250 (8), 2920-32.
24. Kalyanaraman, B.; Felix, C. C.; Sealy, R. C., Peroxidatic oxidation of catecholamines. A kinetic electron spin resonance investigation using the spin stabilization approach. *Journal of Biological Chemistry* 1984, 259 (12), 7584-7589.
25. Won, K.; Kim, Y. H.; An, E. S.; Lee, Y. S.; Song, B. K., Horseradish Peroxidase Catalyzed Polymerization of Cardanol in the Presence of Redox Mediators. *Biomacromolecules* 2003, 5 (1), 1-4.
26. Xu, Y.-P.; Huang, G.-L.; Yu, Y.-T., Kinetics of phenolic polymerization catalyzed by peroxidase in organic media. *Biotechnology and Bioengineering* 1995, 47 (1), 117-119.
27. Tonelli, A. E., Effects of crosslink density and length on the number of intramolecular crosslinks (defects) introduced into a rubbery network. *Polymer* 1974, 15 (4), 194-196.
28. Jin, R.; Hiemstra, C.; Zhong, Z.; Feijen, J., Enzyme-mediated fast in situ formation of hydrogels from dextran-tyramine conjugates. *Biomaterials* 2007, 28 (18), 2791-2800.
29. Park, K.-D.; Joung, Y.-K.; Park, K.-M. In situ Forming Hydrogel and Biomedical Use Thereof 2011 (WO2011/028031).

The invention claimed is:
1. A hyaluronic acid derivative represented by formula (I):

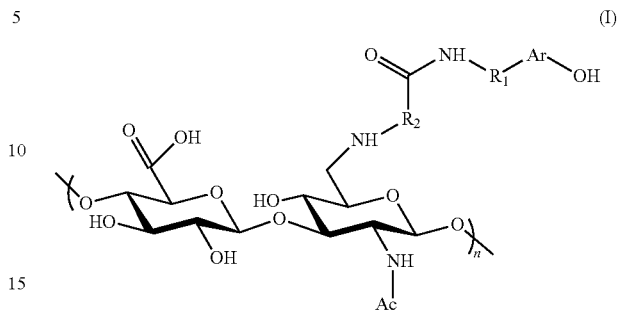

where Ar is phenylene and $R_1$ is ethylene, Ar is 1H-indole-3,5-diyl and $R_1$ is ethylene, or Ar is 1H-indole-3,5-diyl and $R_1$ is carboxyethylene, and where $R_2$ is an alkylene of 3 to 7 carbon atoms, and where n is within the range of 1 to 7500.

2. A method for preparing the hyaluronic acid derivative of formula (I), comprising:
(a) oxidizing the compound represented by the formula (A):

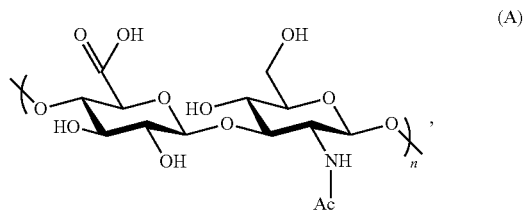

where n is within the range of with 4-acetamido-TEMPO/NaIClO in a protic media to obtain the aldehyde according to the formula (II):

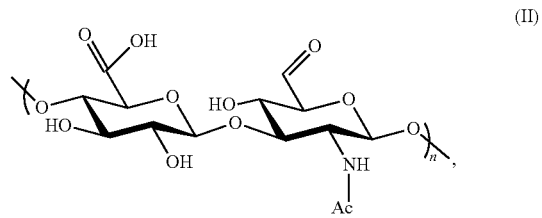

wherein the compound of formula (II) has a substitution degree of 5-15% and a molecular weight within the range of 10000 g/mol to 2000000 g/mol,
(b) then preparing the compound represented by formula (III),

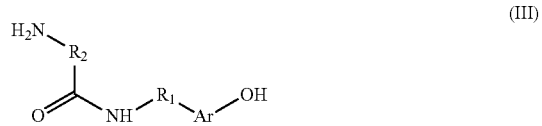

where Ar is phenylene and $R_1$ is ethylene, Ar is 1H-indole-3,5-diyl and $R_1$ is ethylene, or Ar is 1H-indole-3, 5-diyl and $R_1$ is carboxyethylene, and where $R_2$ is an alkylene of 3 to 7 carbon atoms, comprising:

reacting the spacer precursor represented by formula (IV):

$$Z-NH-R_2-COOH \quad (IV),$$

where Z is a primary amino group protecting group, with the ligand represented by formula (V):

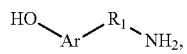

(V)

where Ar is phenylene and $R_1$ is ethylene, Ar is 1H-indole-3,5-diyl and $R_1$ is ethylene, or Ar is 1H-indole-3,5-diyl and $R_1$ is carboxyethylene, and where $R_2$ is an alkylene of 3 to 7 carbon atoms, in an aprotic media at a temperature within the range of 40° C. to 150° C. for 1 to 24 hours in the presence of an agent that activates the carboxylic group of the compound represented by formula (IV), to obtain the compound represented by formula (VI)

$$Z-NH-R_2-CO-NH-R_1-Ar-OH \quad (VI),$$ and removing the protecting group Z, to obtain the compound of formula (III); and (c) reacting the compound of the formula (II) with the compound of formula (III) at a pH within the range of 3 to 8 at room temperature for 1 to 72 hours in the presence of a picoline-borane complex to obtain the derivative according to the formula (I).

3. The method of preparation according to claim 2, wherein the ligand according to the formula (V) is selected from the group consisting of tyramine, serotonin and 5-hydroxytryptophane.

4. The method of preparation according to claim 2 or 3, where Z is tert-butoxycarbonyl and $R_2$ is an alkyl of 3 to 7 carbon atoms in the compound according to the formula (IV).

5. The method of preparation according to claim 2 or 3, wherein the aprotic medium in the reaction of the spacer precursor of formula (IV) with the ligand of formula (V) is THF or DMF and the reaction takes place at the temperature of 50° C. for 2 to 6 hours in the presence of 1,1'-carbodimidazole.

6. The method of preparation according to claim 2 or 3, wherein the removal of the protecting group Z is performed with trifluoroacetic acid or hydrochloric acid.

7. A cross-linked hydrogel obtained by reacting the derivative according to the formula (I)

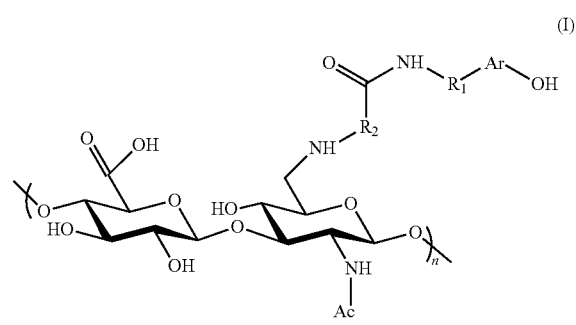

(I)

where Ar is phenylene and $R_1$ is ethylene, or Ar is 1H-indole-3,5-diyl and $H_1$ is ethylene, or Ar is 1H-indole-3,5-diyl and $R_1$ is carboxyethylene, and where $R_2$ is an alkylene of 3 to 7 carbon atoms, and where n is within the range of prepared by the method according to claim 2, with a generator of reactive phenoxy radicals at a pH within the range of 4 to 10, wherein oligomerization of the resultant reactive phenoxy radicals results in crosslinking of the compound of formula (I).

8. A method of production of the hydrogel according to claim 7, comprising reacting the derivative according to formula (I) with a generator of reactive phenoxy radicals at a pH within the range of 4 to 10 wherein oligomerization of the resultant reactive phenoxy radicals results in crosslinking of the compound of formula (I).

9. The method of production according to claim 8, comprising preparing the generator of reactive phenoxy radicals by a method selected from the group consisting of:
(i) reacting horseradish peroxidase with a solution or hydrogen peroxide in water,
(ii) reacting horseradish peroxidase and galactose oxidase with galactose, and (iii) reacting horseradish peroxidase and glucose oxidase with glucose.

* * * * *

UNITED STATES PATENT AND TRADEMARK OFFICE
CERTIFICATE OF CORRECTION

PATENT NO. : 9,492,586 B2
APPLICATION NO. : 14/381091
DATED : November 15, 2016
INVENTOR(S) : Lucie Wolfova et al.

It is certified that error appears in the above-identified patent and that said Letters Patent is hereby corrected as shown below:

On the Title Page

Page 3, Column 1,
Line 52 reads "Description fo Solute" and should read -- Description of Solute --.
Line 56 reads "Description fo Solute" and should read -- Description of Solute --.

Page 3, Column 2,
Line 68 reads "Polyethylene Glycol)-Lipid" and should read -- Poly(ethylene Glycol)-Lipid --.
Line 71 reads "an dnon-toxic" and should read -- and non-toxic --.

Page 6, Column 2,
Line 19 reads "hydrogel fr" and should read -- hydrogels for --.

In the Specification

Column 2,
Line 7 reads "form the protein" and should read -- from the protein --.

Column 6,
Line 48 reads "where $R_2$ is an alkyl having 3 to 7," and should read -- where $R_2$ is an alkyl having 3 to 7 carbons, --.

Column 9,
Line 51 reads "1,1'-carbodiimidazol" and should read -- 1,1'-carbodiimidazole --.

Column 12,
Line 24 reads "8-$CH_2$-hexane acid);" and should read -- δ-$CH_2$-hexane acid); --.
Line 64 reads "1.48 (m, 2 H, (3-$CH_2$-hexane acid);" and should read -- 1.48 (m, 2 H, ß-$CH_2$-hexane acid); --.

Signed and Sealed this
Fourteenth Day of February, 2017

Michelle K. Lee
*Director of the United States Patent and Trademark Office*

CERTIFICATE OF CORRECTION (continued)
U.S. Pat. No. 9,492,586 B2

Column 13,
Line 15 reads "Hylauronan" and should read -- Hyaluronan --.

Column 16,
Line 45 reads "20 ul" and should read -- 20 μl --.
Line 62 reads "10 ul" and should read -- 10 μl --.

Column 17,
Line 56 reads "Youngův" and should read -- Young's --.

In the Claims

Column 20,
Line 38 (Claim 2) reads "within the range of with" and should read -- within the range of 1 to 7500 with --.

Column 21,
Lines 43-44 (Claim 5) read "carbodimidazole" and should read -- carbodiimidazole --.

Column 22,
Line 22 (Claim 7) reads "$H_1$ is ethylene" and should read -- $R_1$ is ethylene --.
Lines 24-25 (Claim 7) read "within the range of prepared by" and should read -- within the range of 1 to 7500 prepared by --.
Line 39 (Claim 9) reads "with a solution or" and should read -- with a solution of --.